(12) United States Patent
Chen et al.

(10) Patent No.: US 12,044,694 B2
(45) Date of Patent: Jul. 23, 2024

(54) METHOD AND SYSTEM FOR ADSORBED PHASE ACTIVITY COEFFICIENTS FOR MIXED-GAS ADSORPTION

(71) Applicant: Texas Tech University System, Lubbock, TX (US)

(72) Inventors: Chau-Chyun Chen, Lubbock, TX (US); Hla Tun, Lubbock, TX (US); Harnoor Kaur, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 672 days.

(21) Appl. No.: 17/286,720

(22) PCT Filed: Oct. 21, 2019

(86) PCT No.: PCT/US2019/057165
§ 371 (c)(1),
(2) Date: Apr. 19, 2021

(87) PCT Pub. No.: WO2020/086439
PCT Pub. Date: Apr. 30, 2020

(65) Prior Publication Data
US 2021/0372902 A1 Dec. 2, 2021

Related U.S. Application Data

(60) Provisional application No. 62/750,165, filed on Oct. 24, 2018.

(51) Int. Cl.
*G01N 7/04* (2006.01)
*G01N 9/26* (2006.01)

(52) U.S. Cl.
CPC ............... *G01N 7/04* (2013.01); *G01N 9/266* (2013.01)

(58) Field of Classification Search
CPC ........... G16C 20/10; G01N 9/266; G01N 7/04
(Continued)

(56) References Cited

U.S. PATENT DOCUMENTS 7,744,842 B2 * 6/2010 Farha .................... B01J 20/226
423/220
2017/0113184 A1 4/2017 Eisenberger

OTHER PUBLICATIONS

Bartholdy S. et al "Capabilities and limitations of predictive engineering theories for multicomponent adsorption," Industrial & Engineering Chemistry Research, vol. 52, pp. 11552-11563, 2013.
(Continued)

*Primary Examiner* — John H Le
(74) *Attorney, Agent, or Firm* — Daniel J. Chalker; Edwin S. Flores; Chalker Flores, LLP

(57) ABSTRACT

A method and system for adsorbed phase activity coefficients for mixed-gas adsorption includes: providing one or more processors, a memory communicably coupled to the one or more processors and an input/output device communicably coupled to the one or more processors; calculating a first gas activity coefficient $\gamma_1$ for a first gas using the one or more processors and a first equation; calculating a second gas activity coefficient $y_2$ for a second gas using the one or more processors and a second equation based on a bulk mole fraction of the first gas; providing the first gas activity coefficient $y_1$ for the first gas and the second gas activity coefficient $y_2$ for the second gas to the input/output device; and using the first gas activity coefficient $y_1$ for the first gas and the second gas activity coefficient $y_2$ for the second gas in the gas adsorption system.

24 Claims, 14 Drawing Sheets

(58) Field of Classification Search
USPC .......................................................... 702/85
See application file for complete search history.

(56) References Cited

OTHER PUBLICATIONS

Calleja G. et al "Pure and multicomponent adsorption equilibrium of carbon dioxide, ethylene, and propane on ZSM-5 zeolites with different Si/Al ratios," Journal of Chemical & Engineering Data, vol. 43, pp. 994-1003, 1998.
Calleja G. et al, "Multicomponent adsorption equilibrium of ethylene, propane, propylene and CO2 on 13X zeolite," Gas separation & purification, vol. 8, pp. 247-256, 1994.
Costa E. et al, "Equilibrium adsorption of methane, ethane, ethylene, and propylene and their mixtures on activated carbon," Journal of Chemical and Engineering Data, vol. 34, pp. 156-160, 1989.
Danner R. P. et al, "Adsorption of carbon monoxide-nitrogen, carbon monoxide-oxygen, and oxygen-nitrogen mixtures on synthetic zeolites," AIChE Journal, vol. 15, pp. 515-520, 1969.
Dubinin M. M. "Fundamentals of the theory of adsorption in micropores of carbon adsorbents: characteristics of their adsorption properties and microporous structures," Pure and Applied Chemistry, vol. 61, pp. 1841-1843, 1989.
Dubinin M. M. i. "Physical adsorption of gases and vapors in micropores," in Progress in surface and membrane science. vol. 9, ed: Elsevier, 1975, pp. 1-70.
Dunne J. et al, "Adsorption of gas mixtures in micropores: effect of difference in size of adsorbate molecules," Chemical engineering science, vol. 49, pp. 2941-2951, 1994.
Hyun S. H. et al, "Equilibrium adsorption of ethane, ethylene, isobutane, carbon dioxide, and their binary mixtures on 13X molecular sieves," Journal of Chemical and Engineering Data, vol. 27, pp. 196-200, 1982.
International Search Report and Written Opinion (PCT/US2019/057165) dated May 1, 2020.
Langmuir, I., "The adsorption of gases on plane surfaces of glass, mica and platinum," Journal of the American Chemical society, vol. 40, pp. 1361-1403, 1918.
Ewis W. K. et al, "Vapor-Adsorbate Equilibrium. II. Acetylene-Ethylene on Activated Carbon and on Silica Gel," Journal of the American Chemical Society, vol. 72, pp. 1157-1159, 1950.
Ewis W. K. et al, "Vapor-Adsorbate Equilibrium. III. The Effect of Temperature on the Binary Systems Ethylene-Propane, Ethylene-Propylene over Silica Gel," Journal of the American Chemical Society, vol. 72, pp. 1160-1163, 1950.
Lewis W. K. et al, "Vapor-adsorbate1 equilibrium. I. propane-propylene on activated carbon and on silica gel," Journal of the American Chemical Society, vol. 72, pp. 1153-1157, 1950.
Markham E. C. et al, "The adsorption of gas mixtures by silica," Journal of the American Chemical Society, vol. 53, pp. 497-507, 1931.
Martinez A. et al, "Predicting adsorption isotherms using a two-dimensional statistical associating fluid theory," The Journal of chemical physics, vol. 126, p. 074707, 2007.
Myers A. L. "Activity coefficients of mixtures adsorbed on heterogeneous surfaces," AIChE journal, vol. 29, pp. 691-693, 1983.
Myers A. L. et al, "Thermodynamics of mixed-gas adsorption," AIChE Journal, vol. 11, pp. 121-127, 1965.
Nolan J. T. "Equilibrium adsorption of oxygen, nitrogen, carbon monoxide, and their binary mixtures on molecular sieve type 10X," Journal of Chemical and Engineering Data, vol. 26, pp. 112-115, 1981.
Polanyi M, "Adsorption von Gasen (Dampfen) durch ein festes nichtfluchtiges Adsorbens," Verhandlungen der Deutschen Physekalischen Gesellschaft, vol. 18, pp. 55-80, 1916.
Ravichandran A. et al, "Predicting NRTL binary interaction parameters from molecular simulations," AIChE Journal, 2018.
Renon H. et al, "Local compositions in thermodynamic excess functions for liquid mixtures," AIChE journal, vol. 14, pp. 135-144, 1968.
Ruthven D. M. "Simple theoretical adsorption isotherm for zeolites," Nature Physical Science, vol. 232, p. 70, 1971.
Sakuth M. et al, "Measurement and prediction of binary adsorption equilibria of vapors on dealuminated Y-zeolites (DAY)," Chemical Engineering and Processing: Process Intensification, vol. 37, pp. 267-277, 1998.
Scott R. L. "Corresponding states treatment of nonelectrolyte solutions," The Journal of Chemical Physics, vol. 25, pp. 193-205, 1956.
Shapiro A. A. et al, "Potential theory of multicomponent adsorption," Journal of Colloid and Interface Science, vol. 201, pp. 146-157, 1998.
Siperstein F. R. "Mixed-gas adsorption," AIChE journal, vol. 47, pp. 1141-1159, 2001.
Sircar S. et al, "Surface potential theory of multilayer adsorption from gas mixtures," Chemical Engineering Science, vol. 28, pp. 489-499, 1973.
Sochard S. et al, "Modeling of adsorption isotherm of a binary mixture with real adsorbed solution theory and nonrandom two-liquid model," AIChE journal, vol. 56, pp. 3109-3119, 2010.
Steffan D. G. et al, "Thermodynamic modeling of binary and ternary adsorption on silica gel," AIChE journal, vol. 47, pp. 1234-1246, 2001.
Suwanayuen S. et al, "Vacancy solution theory of adsorption from gas mixtures," AIChE Journal, vol. 26, pp. 76-83, 1980.
Talu O. et al, "Multicomponent adsorption equilibria of nonideal mixtures," AIChE journal, vol. 32, pp. 1263-1276, 1986.
Talu O. et al, "Spreading pressure dependent equation for adsorbate phase activity coefficients," Reactive Polymers, on Exchangers, Sorbents, vol. 5, pp. 81-91, 1987.
Walton K. S. et al, "Predicting multicomponent adsorption: 50 years of the ideal adsorbed solution theory," AIChE Journal, vol. 61, pp. 2757-2762, 2015.
Talu, Orhan et al. "Activity Coefficients of Adsorbed Mixtures" Adsorption, vol. 1, pp. 103-112 (Jan. 1, 1995).

* cited by examiner

1302 — Provide one or more processors, a memory communicably coupled to the one or more processors and an input/output device communicably coupled to the one or more processors 1304 — Calculate a first gas activity coefficient $\gamma_1$ for a first gas using the one or more processors and a first equation comprising $$\ln \gamma_1 = \frac{x_2^2 \tau_{12}[\exp(-\alpha\tau_{12})-1]}{[x_1\exp(-\alpha\tau_{12})+x_2]^2}$$

1306 — Calculate a second gas activity coefficient $\gamma_2$ for a second gas using the one or more processors and a second equation comprising $$\ln \gamma_2 = \frac{x_1^2 \tau_{21}[\exp(-\alpha\tau_{21})-1]}{[x_1+x_2\exp(-\alpha\tau_{21})]^2}$$

1308 — Provide the first gas activity coefficient $\gamma_1$ for the first gas and the second gas activity coefficient $\gamma_2$ for the second gas to the input/output device 1310 — Use the first gas activity coefficient $\gamma_1$ for the first gas and the second gas activity coefficient $\gamma_2$ for the second gas in the gas adsorption system wherein: $x_1$ is a bulk mole fraction of the first gas,
$x_2$ is a bulk mole fraction of the second gas,
$\alpha$ is a first adjustable parameter,
$\tau_{12}$ is derived by regression from mixture isotherm data and reflects a difference between adsorbate-adsorbent interactions of the first gas and the second gas, and $\tau_{12} = -\tau_{21} = \left(\frac{g_{10}-g_{20}}{RT}\right)$,
$g_{10}$ is an interaction energy between molecules of the first gas and an adsorbent adsorption site,
$g_{20}$ is an interaction energy between molecules of the second gas and an adsorbent adsorption site,
$R$ is the gas constant, and
$T$ is a temperature for the gas adsorption system.

FIG. 13

METHOD AND SYSTEM FOR ADSORBED PHASE ACTIVITY COEFFICIENTS FOR MIXED-GAS ADSORPTION

CROSS-REFERENCE TO RELATED APPLICATIONS

This application is the National Stage of International Application No. PCT/US2019/057165, filed on Oct. 21, 2019, which claims priority to U.S. Provisional Application Ser. No. 62/750,165, filed Oct. 24, 2018. The contents of both applications are incorporated by reference herein in their entirety.

STATEMENT OF FEDERALLY FUNDED RESEARCH

Funding support is provided by the U.S. Department of Energy under the grant DE-EE0007888-02-7.

TECHNICAL FIELD OF THE INVENTION

The present invention relates in general to non-ideal mixed gas adsorption. In particular, the present invention relates to a method and system for adsorbed phase activity coefficients for mixed-gas adsorption.

BACKGROUND OF THE INVENTION

Without limiting the scope of the invention, its background is described in connection with local composition activity coefficients for mixed-gas adsorption for two gases.

The cornerstone of any gas adsorption system design is the accuracy of the vapor-adsorbate equilibrium (VAE) predictions. The multicomponent Langmuir isotherm equation [1], while useful for extracting insight into the fundamental thermodynamics of adsorption, cannot provide predictions with sufficient accuracy for rigorous adsorption design for systems of industrial interest, such as air separation, nitrogen rejection from methane, and carbon dioxide capture [2]. Beyond the multicomponent Langmuir isotherm equation, many theoretical models have been proposed to describe multicomponent adsorption, broadly classified here as solution theories [3-6], potential theories [7-10], and statistical theories [11, 12]. However, these models often become unwieldy and difficult for practicing engineers to comprehend and use, and are largely confined to academic and industrial research interests. Among them, solution theories are the most likely candidates for general use by practicing engineers due to their similarity to traditional vapor-liquid equilibria (VLE) calculations in classical thermodynamics.

Myers and Prausnitz [3] used classical surface thermodynamics to develop the Ideal Adsorbed Solution Theory (IAST), which to this date is considered the benchmark for modeling mixture adsorption isotherms [13]. The authors assume the adsorbate phase behaves as an ideal solution at constant spreading pressure ($\pi$) in equilibrium with an ideal gas phase, resulting in a Raoult's law type expression given by Eq. 1.

$$y_i P = x_i P_i^0(\pi) \tag{1}$$

In Eq. 1, P is the total system pressure, $y_i$ and $x_i$ are the mole fractions of component i in the gas and the adsorbate phase, respectively, and $P_i^0$ is the equilibrium gas phase pressure of the pure component i at the same temperature and spreading pressure as the adsorbed mixture. IAST is known to work well for chemically similar molecules of similar size, but IAST fails to predict the adsorption equilibria of polar gas mixtures, such as $O_2$—CO and $CO_2$—$C_3H_8$ binaries, and for heterogeneous adsorbents like molecular sieves or metal organic frameworks (MOFs) [13].

Deviations from IAST behavior are typically negative, as shown by Myers and coworkers for the adsorption of mixtures on heterogeneous surfaces [14, 15]. The Real Adsorbed Solution Theory (RAST) was proposed to account for the non-ideality during adsorption [14, 16-19]. In analogy with the treatment of non-ideal solutions in VLE, the modified Raoult's law type expression in RAST can be written as Eq. 2.

$$y_i P = x_i \gamma_i(x_i, \pi) P_i^0(\pi) \tag{2}$$

In Eq. 2, $\gamma_i$ is the activity coefficient of the adsorbate species i, which reflects the non-ideality of the adsorbate phase. Similar to VLE, the activity coefficient is defined as the ratio of the fugacity of the component in the real adsorbate mixture and the fugacity at a reference state, usually taken to be the pure adsorbate at the same temperature and spreading pressure as the mixture and is therefore a function of pressure [17, 20].

Various well known activity coefficient models such as Van Laar, Wilson, NRTL, and UNIQUAC [16-19] have been used to calculate the activity coefficients of the adsorbate phase components. However, these popular activity coefficient models were developed for bulk liquids and they do not properly account for the unique adsorbate-adsorbent interactions present in the adsorption systems. Consequently, these models fail to correlate mixture isotherm data properly; the regressed model binary interaction parameters lack physical significance; the model extrapolations for multi-component systems are not to be trusted [17, 20]. To address these issues, this study presents a novel activity coefficient expression that properly takes into consideration the effect of adsorbate-adsorbent interactions with the non-random two-liquid (NRTL) theory of Renon and Prausnitz [21].

Methods and systems for identifying local composition activity coefficients for mixed-gas adsorption are desirable.

SUMMARY OF THE INVENTION

Taking into consideration the adsorbate-adsorbent interactions, a novel activity coefficient model is derived from the non-random two-liquid theory for mixed-gas adsorption equilibrium. In contrast with the conventional activity coefficient models developed for bulk liquids, the new model correctly predicts negative deviations from ideality for adsorbed gas mixtures and azeotropic behavior exhibited by selected gas-adsorbent systems. Requiring a single binary interaction parameter per adsorbate-adsorbate pair, the model successfully correlates wide varieties of gas adsorption isotherm data and it is a powerful engineering thermodynamic tool in correlating and predicting multicomponent adsorption isotherms.

In some embodiments of the disclosure, a computerized method for identifying activity coefficients for mixed-gas adsorption equilibrium in a gas adsorption system includes: providing one or more processors, a memory communicably coupled to the one or more processors and an input/output device communicably coupled to the one or more processors; calculating a first gas activity coefficient $\gamma_1$ for a first gas using the one or more processors and a first equation comprising $$\ln\gamma_1 = \frac{x_2^2 \tau_{12}[\exp(-\alpha\tau_{12}) - 1]}{[x_1 \exp(-\alpha\tau_{12}) + x_2]^2};$$

calculating a second gas activity coefficient $\gamma_2$ for a second gas using the one or more processors and a second equation comprising $$\ln\gamma_2 = \frac{x_1^2 \tau_{21}[\exp(-\alpha\tau_{21}) - 1]}{[x_1 + x_2\exp(-\alpha\tau_{21})]^2};$$

wherein: $x_1$ is a bulk mole fraction of the first gas, $x_2$ is a bulk mole fraction of the second gas, $\alpha$ is a first adjustable parameter, $\tau_{12}$ is derived by regression from mixture isotherm data and reflects a difference between adsorbate-adsorbent interactions of the first gas and the second gas, and $$\tau_{12} = -\tau_{21} = \left(\frac{g_{10} - g_{20}}{RT}\right),$$

$g_{20}$ is an interaction energy between molecules of the first gas and an adsorbent adsorption site, $g_{20}$ is an interaction energy between molecules of the second gas and an adsorbent adsorption site, R is the gas constant, and T is a temperature for the gas adsorption system; providing the first gas activity coefficient $\gamma_1$ for the first gas and the second gas activity coefficient $\gamma_2$ for the second gas to the input/output device; and using the first gas activity coefficient $\gamma_1$ for the first gas and the second gas activity coefficient $\gamma_2$ for the second gas in the gas adsorption system. In one aspect, the first gas or the second gas is polar. In another aspect, the first gas is $C_2H_4$ and the second gas is $C_2H_6$; the first gas is $C_2H_4$ and the second gas is $C_3H_6$; the first gas is $CO_2$ and the second gas is $C_2H_4$; or the first gas is $O_2$ and the second gas is $N_2$. In another aspect, the adsorbent adsorption site comprises activated carbon, silica gel, zeolite molecular sieve 13X, or zeolite molecular sieve 10X. In another aspect, the temperature is from 273 K to 323 K. In another aspect, a pressure for the gas adsorption system is from 10 kPa to 102 kPa. In another aspect, the gas adsorption system comprises an air separation system, a nitrogen rejection from methane system, or a carbon dioxide capture system. In another aspect, the input/output device comprises an interface to the gas adsorption system.

In some embodiments of the disclosure, a non-transitory computer readable medium containing program instructions that cause one or more processors to perform a method for identifying activity coefficients for mixed-gas adsorption equilibrium in a gas adsorption system includes: calculating a first gas activity coefficient $\gamma_1$ for a first gas using a first equation comprising $$\ln\gamma_1 = \frac{x_2^2 \tau_{12}[\exp(-\alpha\tau_{12}) - 1]}{[x_1 \exp(-\alpha\tau_{12}) + x_2]^2};$$

calculating a second gas activity coefficient $\gamma_2$ for a second gas using a second equation comprising $$\ln\gamma_2 = \frac{x_1^2 \tau_{21}[\exp(-\alpha\tau_{21}) - 1]}{[x_1 + x_2\exp(-\alpha\tau_{21})]^2};$$

wherein: $x_1$ is a bulk mole fraction of the first gas, $x_2$ is a bulk mole fraction of the second gas, $\alpha$ is a first adjustable parameter, $\tau_{12}$ is derived by regression from mixture isotherm data and reflects a difference between adsorbate-adsorbent interactions of the first gas and the second gas, and $$\tau_{12} = -\tau_{21} = \left(\frac{g_{10} - g_{20}}{RT}\right),$$

$g_{10}$ is an interaction energy between molecules of the first gas and an adsorbent adsorption site, $g_{20}$ is an interaction energy between molecules of the second gas and an adsorbent adsorption site, R is the gas constant, and T is a temperature for the gas adsorption system; providing the first gas activity coefficient $\gamma_1$ for the first gas and the second gas activity coefficient $\gamma_2$ for the second gas to an input/output device communicably coupled to the one or more processors; and using the first gas activity coefficient $\gamma_1$ for the first gas and the second gas activity coefficient $\gamma_2$ for the second gas in the gas adsorption system. In one aspect, the first gas or the second gas is polar. In another aspect, the first gas is $C_2H_4$ and the second gas is $C_2H_6$; the first gas is $C_2H_4$ and the second gas is $C_3H_6$; the first gas is $CO_2$ and the second gas is $C_2H_4$; or the first gas is $O_2$ and the second gas is $N_2$. In another aspect, the adsorbent adsorption site comprises activated carbon, silica gel, zeolite molecular sieve 13X, or zeolite molecular sieve 10X. In another aspect, the temperature is from 273 K to 323 K. In another aspect, a pressure for the gas adsorption system is from 10 kPa to 102 kPa. In another aspect, the gas adsorption system comprises an air separation system, a nitrogen rejection from methane system, or a carbon dioxide capture system. In another aspect, the input/output device comprises an interface to the gas adsorption system.

In some embodiments of the disclosure, a system for identifying activity coefficients for mixed-gas adsorption equilibrium in a gas adsorption system includes: a memory; an input/output device; and one or more processors communicably coupled to the memory and the input/output device, wherein the one or more processors: calculate a first gas activity coefficient $\gamma_1$ for a first gas using the one or more processors and a first equation comprising $$\ln\gamma_1 = \frac{x_2^2 \tau_{12}[\exp(-\alpha\tau_{12}) - 1]}{[x_1 \exp(-\alpha\tau_{12}) + x_2]^2};$$

calculate a second gas activity coefficient $\gamma_2$ for a second gas using the one or more processors and a second equation comprising $$\ln\gamma_2 = \frac{x_1^2 \tau_{21}[\exp(-\alpha\tau_{21}) - 1]}{[x_1 + x_2\exp(-\alpha\tau_{21})]^2};$$

wherein: $x_1$ is a bulk mole fraction of the first gas, $x_2$ is a bulk mole fraction of the second gas, $\alpha$ is a first adjustable parameter, $\tau_{12}$ is derived by regression from mixture isotherm data and reflects a difference between adsorbate-adsorbent interactions of the first gas and the second gas, and $$\tau_{12} = -\tau_{21} = \left(\frac{g_{10} - g_{20}}{RT}\right),$$

$g_{10}$ is an interaction energy between molecules of the first gas and an adsorbent adsorption site, $g_{20}$ is an interaction energy between molecules of the second gas and an adsorbent adsorption site, R is the gas constant, and T is a temperature for the gas adsorption system; provide the first gas activity coefficient $\gamma_1$ for the first gas and the second gas activity coefficient $\gamma_2$ for the second gas to the input/output device; and use the first gas activity coefficient $\gamma_1$ for the first gas and the second gas activity coefficient $\gamma_2$ for the second gas in the gas adsorption system. In one aspect, the first gas or the second gas is polar. In another aspect, the first gas is $C_2H_4$ and the second gas is $C_2H_6$; the first gas is $C_2H_4$ and the second gas is $C_3H_6$; the first gas is $CO_2$ and the second gas is $C_2H_4$; or the first gas is $O_2$ and the second gas is $N_2$. In another aspect, the adsorbent adsorption site comprises activated carbon, silica gel, zeolite molecular sieve 13X, or zeolite molecular sieve 10X. In another aspect, the temperature is from 273 K to 323 K. In another aspect, a pressure for the gas adsorption system is from 10 kPa to 102 kPa. In another aspect, the gas adsorption system comprises an air separation system, a nitrogen rejection from methane system, or a carbon dioxide capture system. In another aspect, the input/output device comprises an interface to the gas adsorption system.

In addition to the foregoing, various other method, system, and apparatus aspects are set forth in the teachings of the present disclosure, such as the claims, text, and drawings forming a part of the present disclosure.

The foregoing is a summary and thus contains, by necessity, simplifications, generalizations, and omissions of detail. Consequently, those skilled in the art will appreciate that this summary is illustrative only and is not intended to be in any way limiting. There aspects, features, and advantages of the devices, processes, and other subject matter described herein will be become apparent in the teachings set forth herein.

BRIEF DESCRIPTION OF THE DRAWINGS

For a more complete understanding of the features and advantages of the present invention, reference is now made to the detailed description of the invention along with the accompanying figures, in which.

and the real case scenario $$\left(\frac{\pi A}{RT}\right)_{RAST}$$

for an equimolar $C_2H_6$ (1)-$C_3H_6$ (2) mixture from the pure component isotherms on activated carbon [26] at 323 K and 10 kPa, $\tau_{12}$=1.515.

Figure 5A:
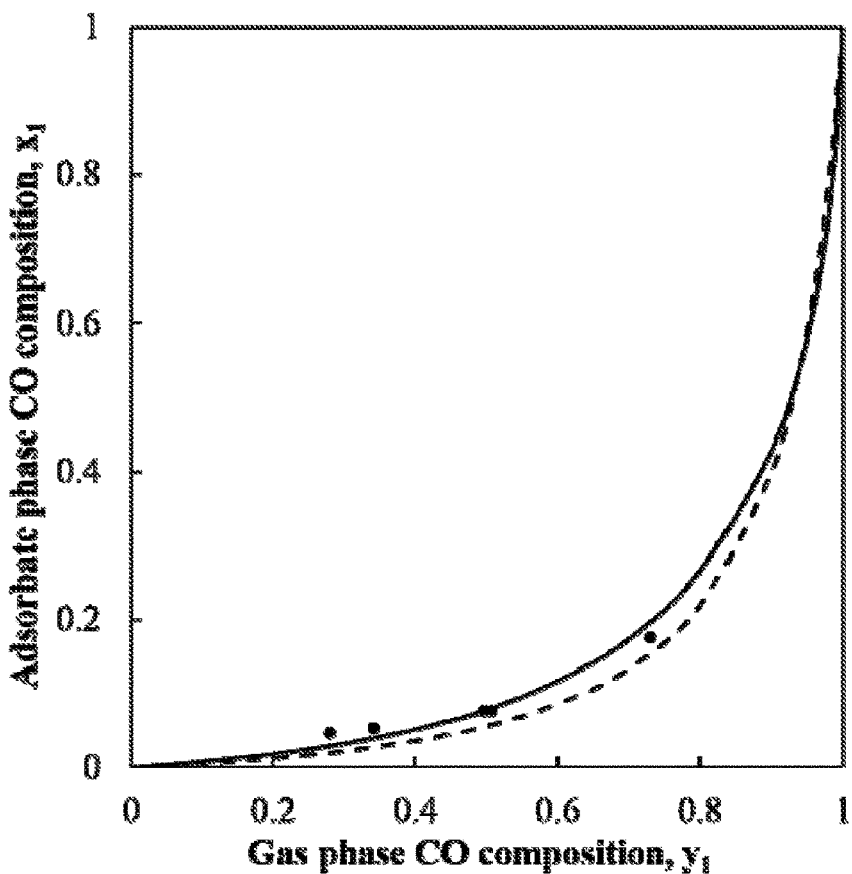

FIG. 5A is a graph comparing the experimental isotherm data [31] for CO(1)-$CO_2$(2) binary mixture at 373 K and 101.3 kPa with IAST and RAST results.

Figure 5B:
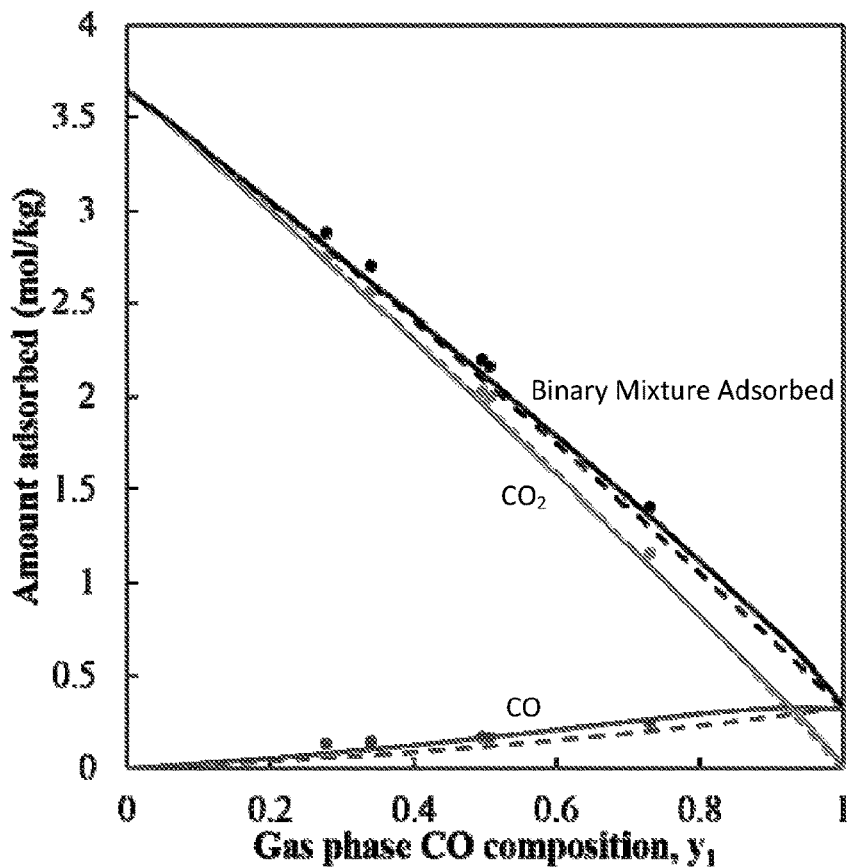

FIG. 5B is a graph comparing the experimental amount adsorbed [31] for CO(1)-$CO_2$(2) and total amount of the binary mixture adsorbed on silica gel at 373 K and 101.3 kPa with IAST and RAST results.

Figure 6A:
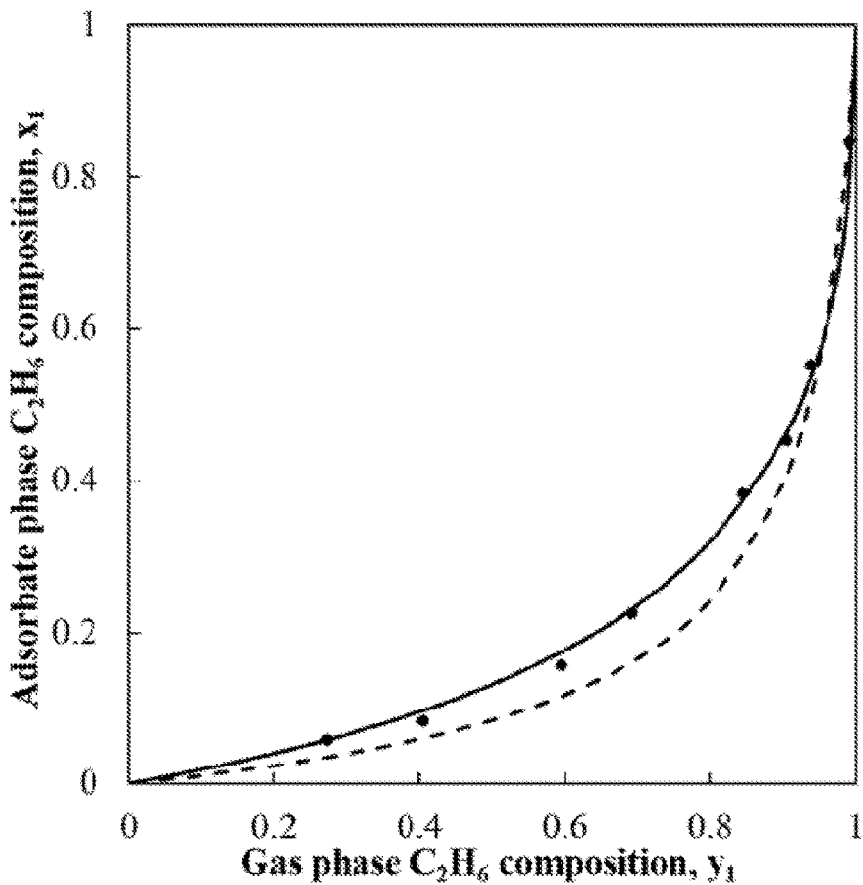

FIG. 6A is a graph comparing experimental equilibrium data [26] of adsorbed $C_2H_6$(1)-$C_3H_6$(2) binary mixture on activated carbon at 323 K and 10 kPa with IAST and RAST results.

Figure 6B:
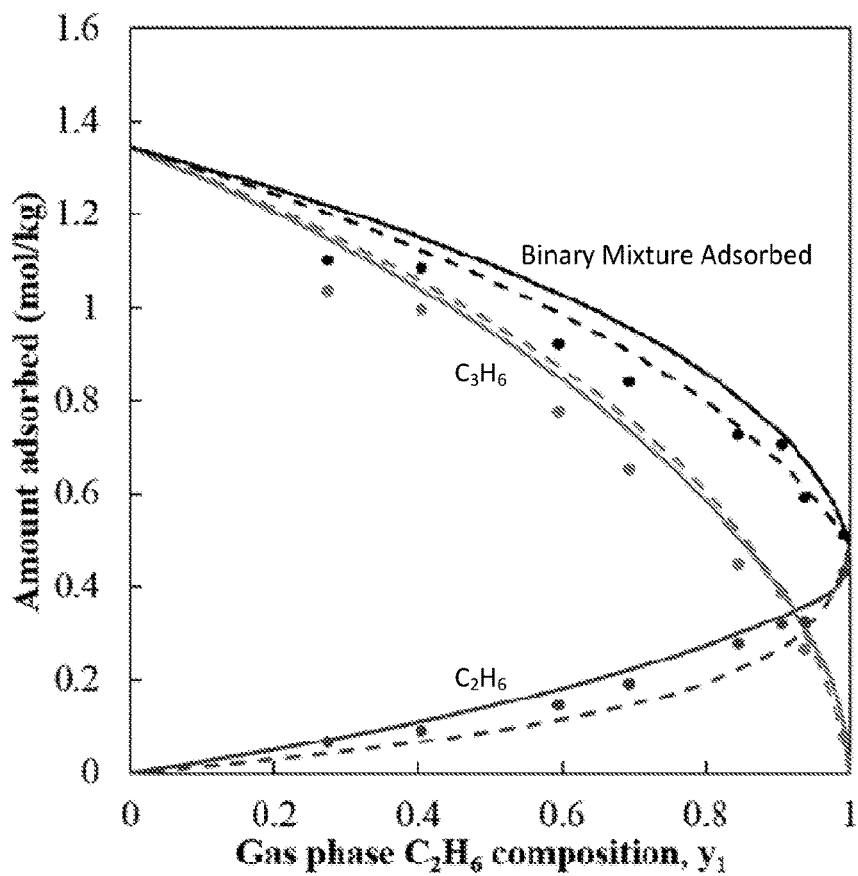

FIG. 6B is a graph comparing experimental measurement of amount adsorbed [26] for $C_2H_6$(1)-$C_3H_6$(2) and total amount of the binary mixture adsorbed on activated carbon at 323 K and 10 kPa with IAST and RAST results.

Figure 7A:
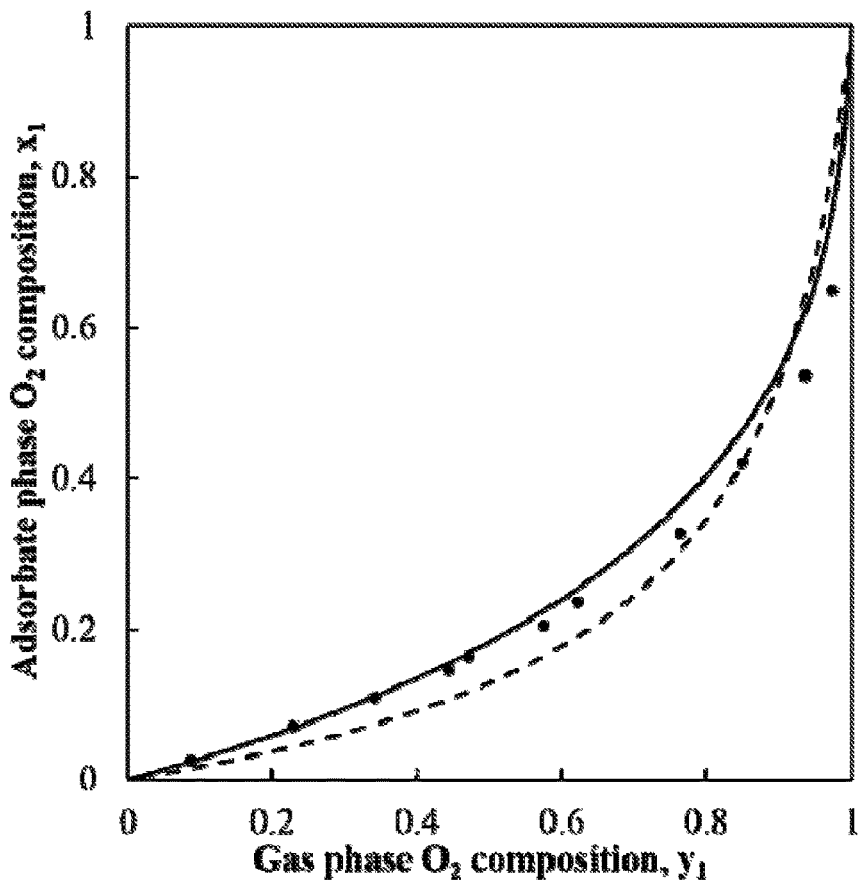

FIG. 7A is a graph comparing the experimental equilibrium data [32] for $O_2$(1)-$N_2$(2) binary mixture on zeolite molecular sieve (ZSM)-5A at 144 K and 101.325 kPa with IAST and RAST model results.

Figure 7B:
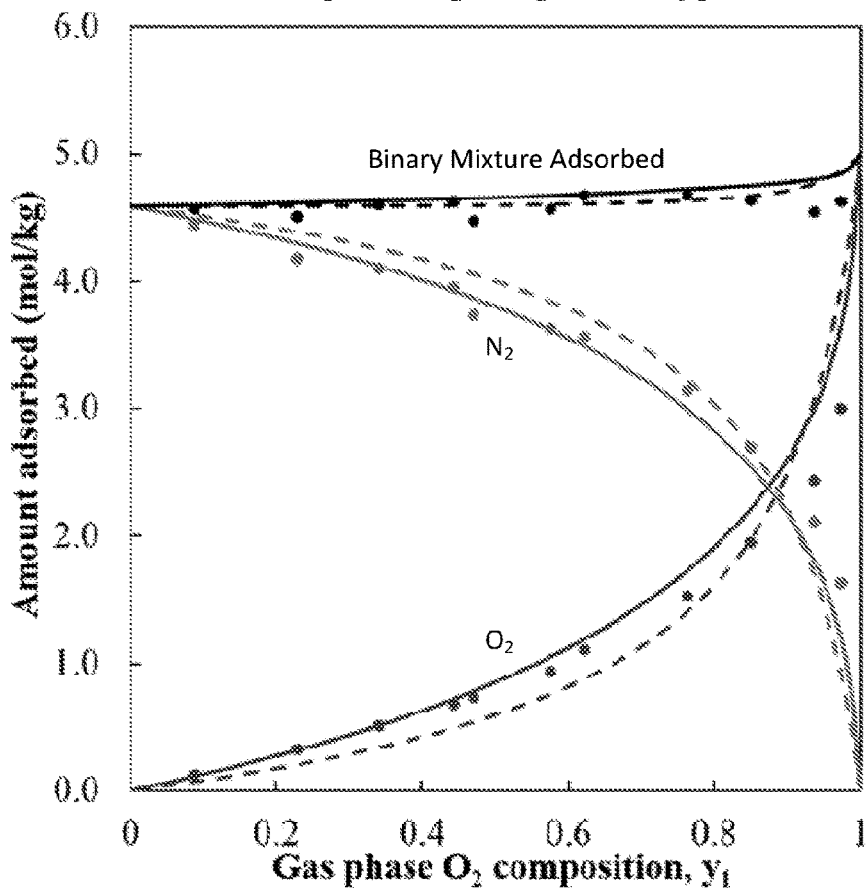

FIG. 7B is a graph comparing the experimental amount adsorbed [32] for $O_2$(1)-$N_2$(2) and the total amount of the binary mixture adsorbed on zeolite molecular sieve (ZSM)-5A at 144 K and 101.325 kPa with IAST and RAST model results.

Figure 8A:
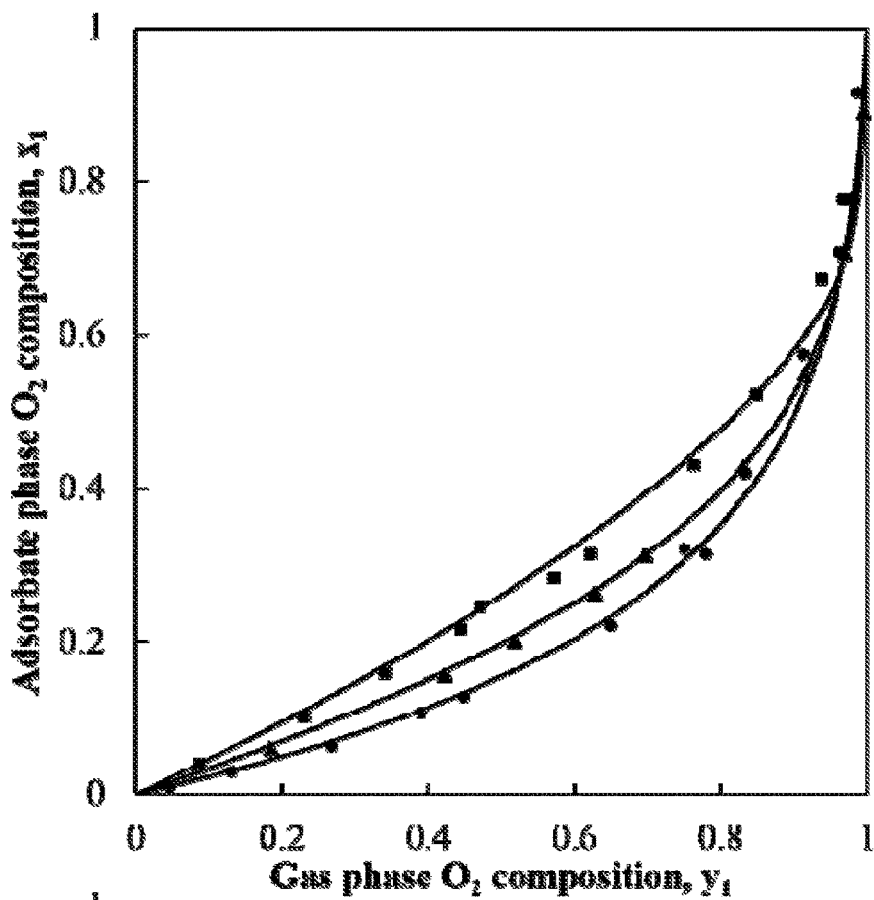

FIG. 8A is a graph comparing the experimental equilibrium data of adsorbed $O_2$(1)-$N_2$(2) binary on zeolite 10X at 144 K, 172 K and 227 K, and 101.325 kPa with RAST model results on zeolite 10X.

Figure 8B:
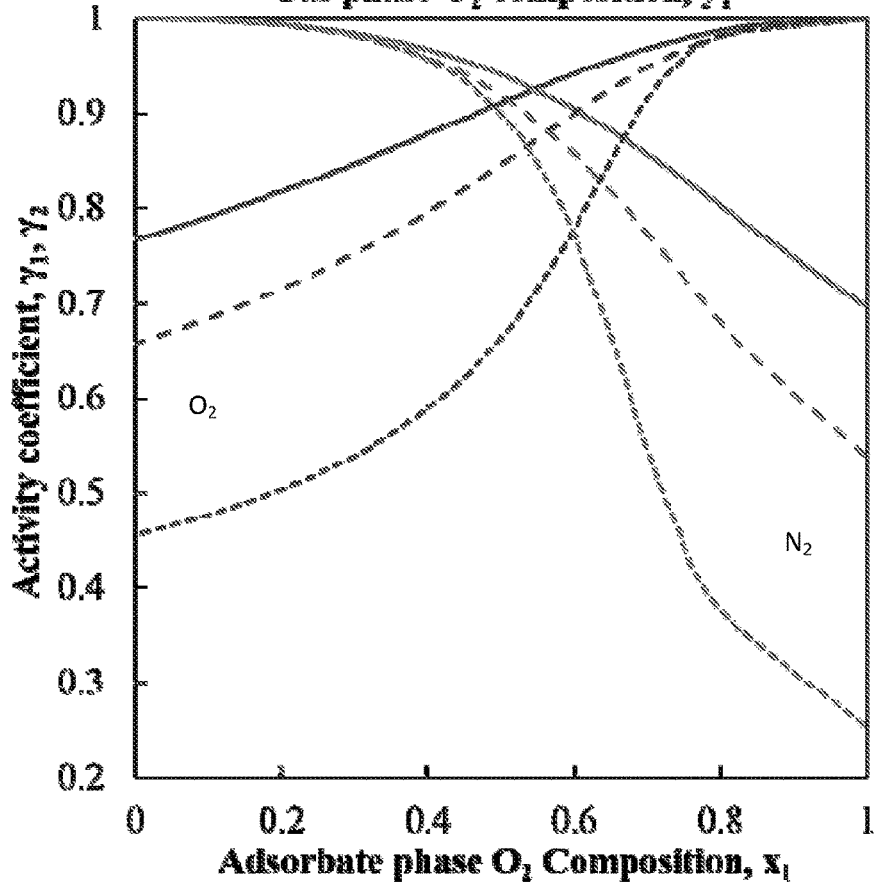

FIG. 8B is a graph showing the activity coefficients of adsorbed $O_2$—$N_2$ binary mixture on zeolite 10X at 144 K, 172 K and 227 K, and 101.325 kPa.

Figure 8C:
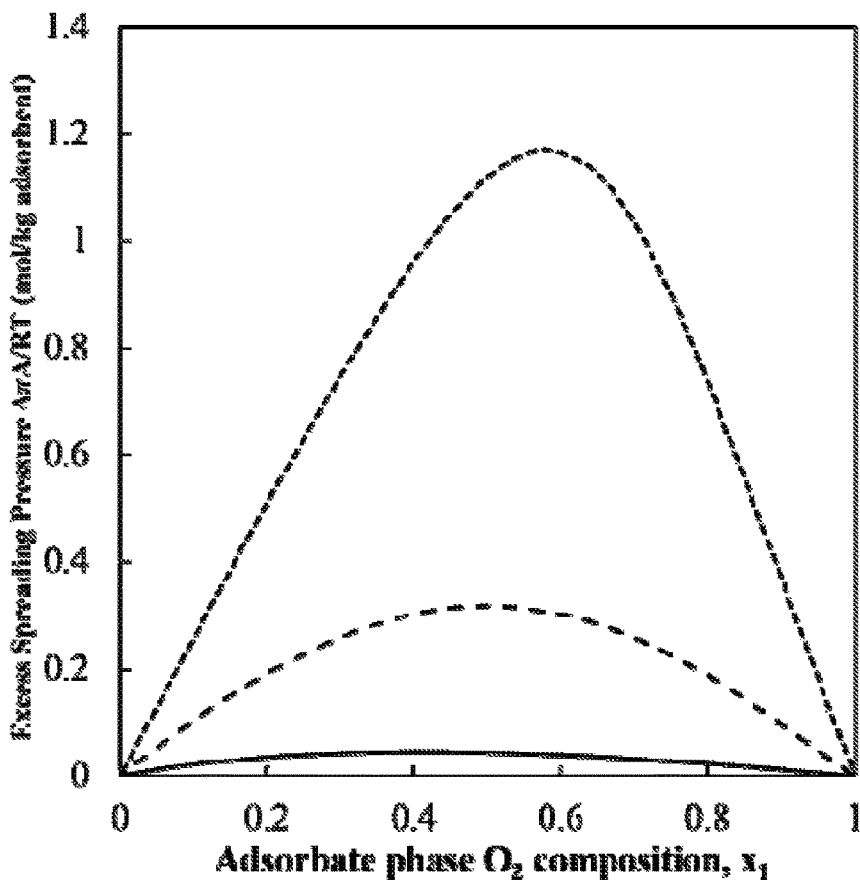

FIG. 8C is a graph showing the excess spreading pressure of the adsorbed $O_2$(1)-$N_2$(2) binary mixture on zeolite 10X at 144 K, 172 K and 227 K, and 101.325 kPa.

Figure 9A:
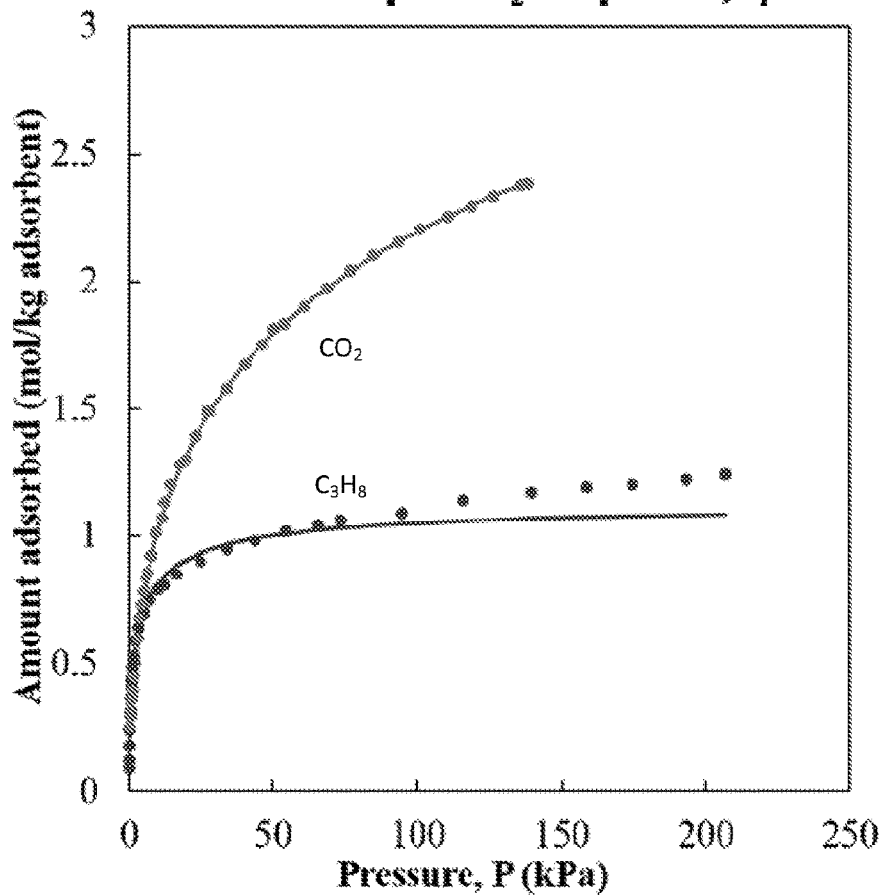

FIG. 9A is a graph comparing experimental pure component adsorption isotherm data [17] of $C_3H_8$(1) and $CO_2$(2) on zeolite H-Mordenite at 303 K with Sips isotherm correlations.

Figure 9B:
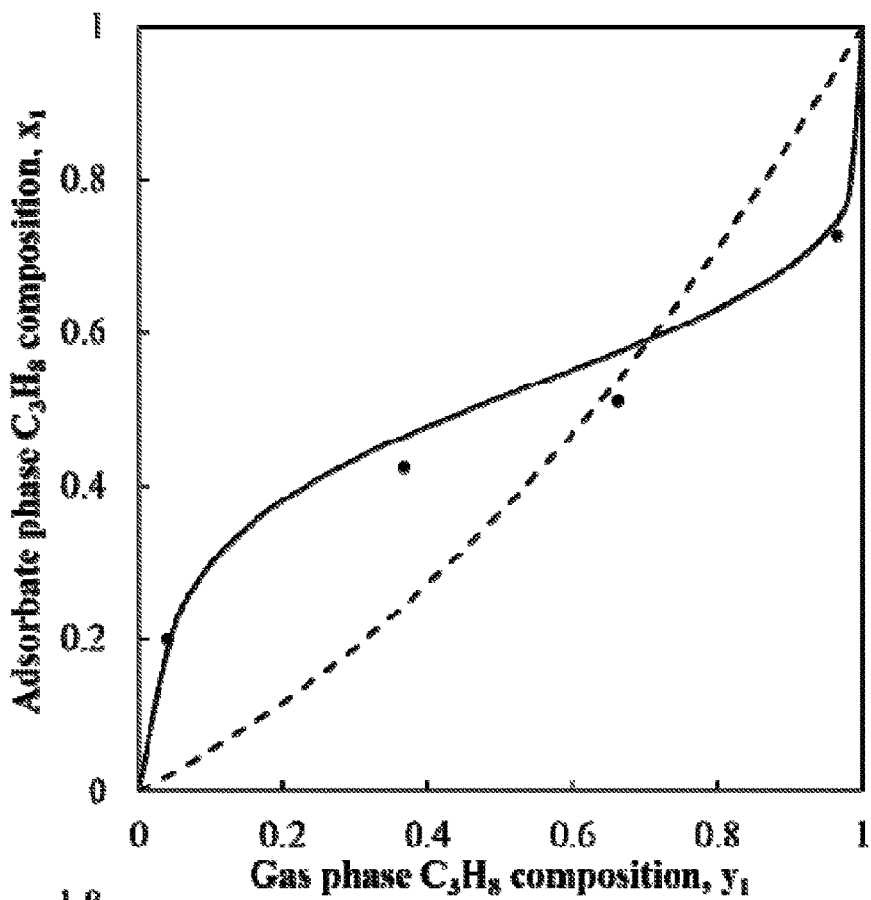

FIG. 9B is a graph comparing experimental equilibrium data [17] of adsorbed $C_3H_8$(1)-$CO_2$(2) binary mixture on zeolite H-Mordenite at 303 K and 41 kPa with IAST and RAST model results.

Figure 9C:
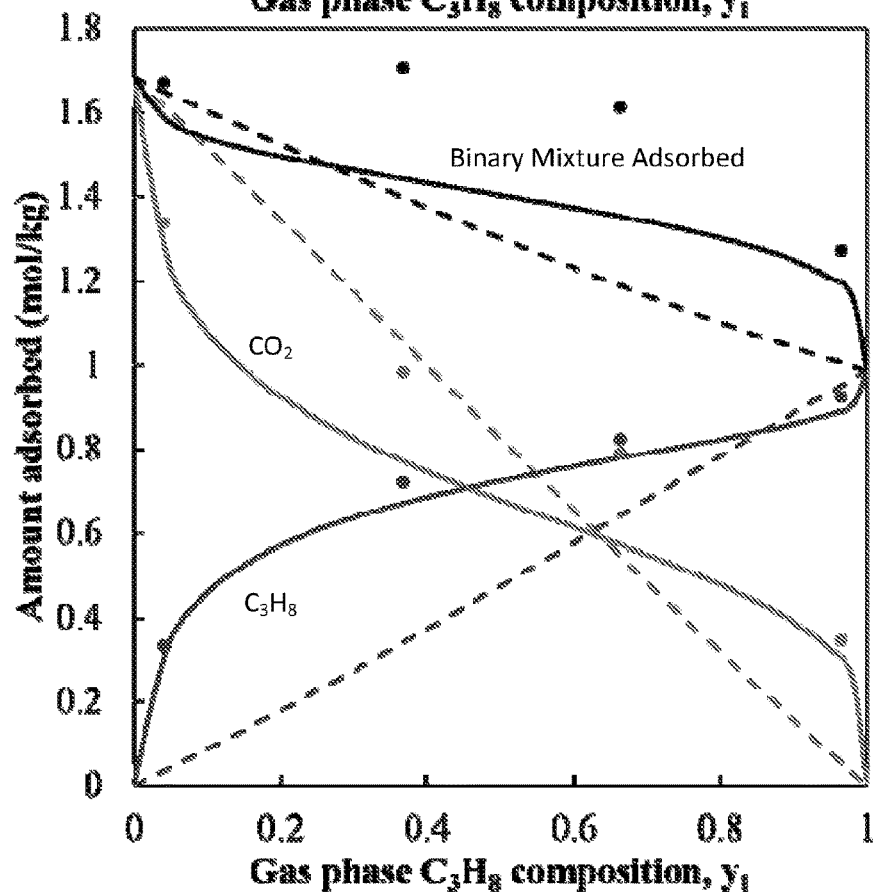

FIG. 9C is a graph comparing the experimental measurement of amount adsorbed [17] for $C_3H_8$(1)-$CO_2$(2) and total amount of the binary mixture adsorbed on zeolite H-Mordenite at 303 K and 41 kPa with IAST and RAST model results.

Figure 10A:
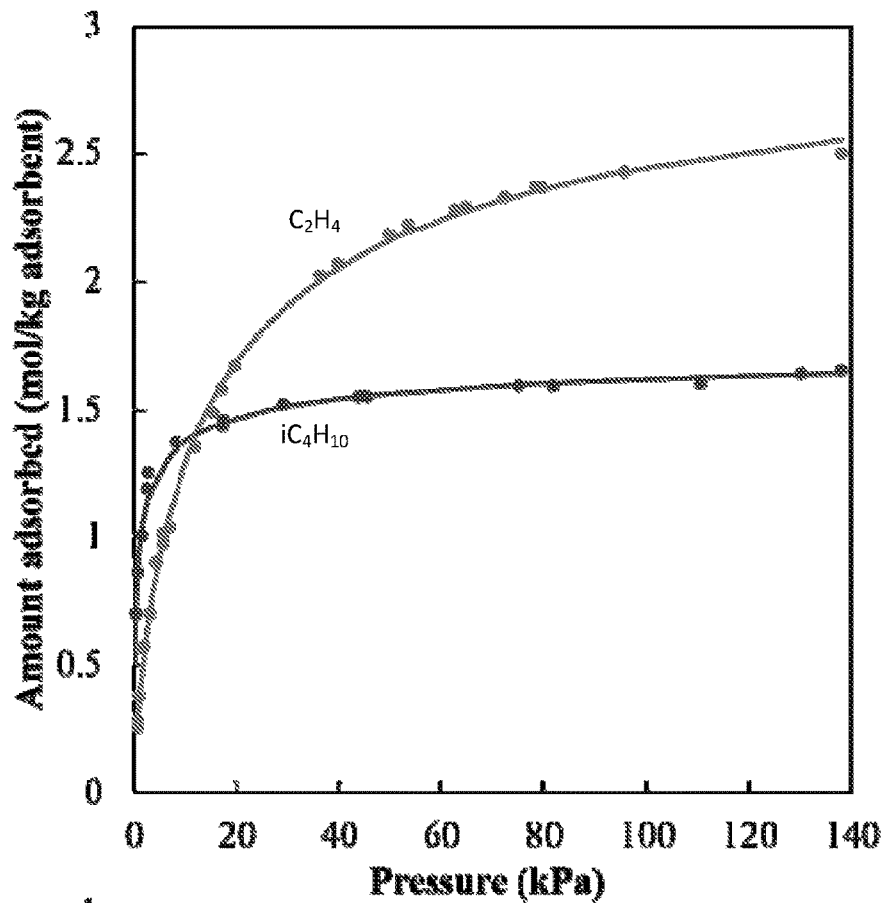

FIG. 10A is a graph comparing experimental pure component adsorption isotherm data [35] of $iC_4H_{10}$(1) and $C_2H_4$(2) on zeolite 13X at 323 K with Sips isotherm correlations.

Figure 10B:
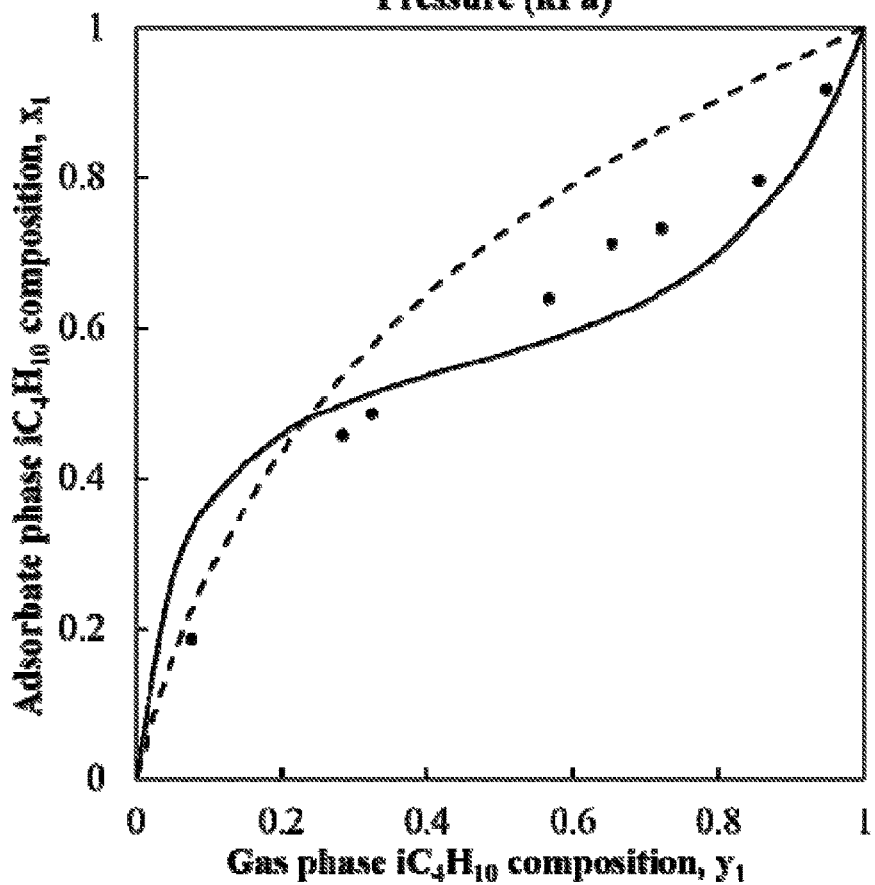

FIG. 10B is a graph comparing experimental equilibrium data [35] of adsorbed $iC_4H_{10}$(1)-$C_2H_4$(2) binary mixture on zeolite 13X at 323 K and 137.8 kPa with IAST and RAST results.

Figure 10C:
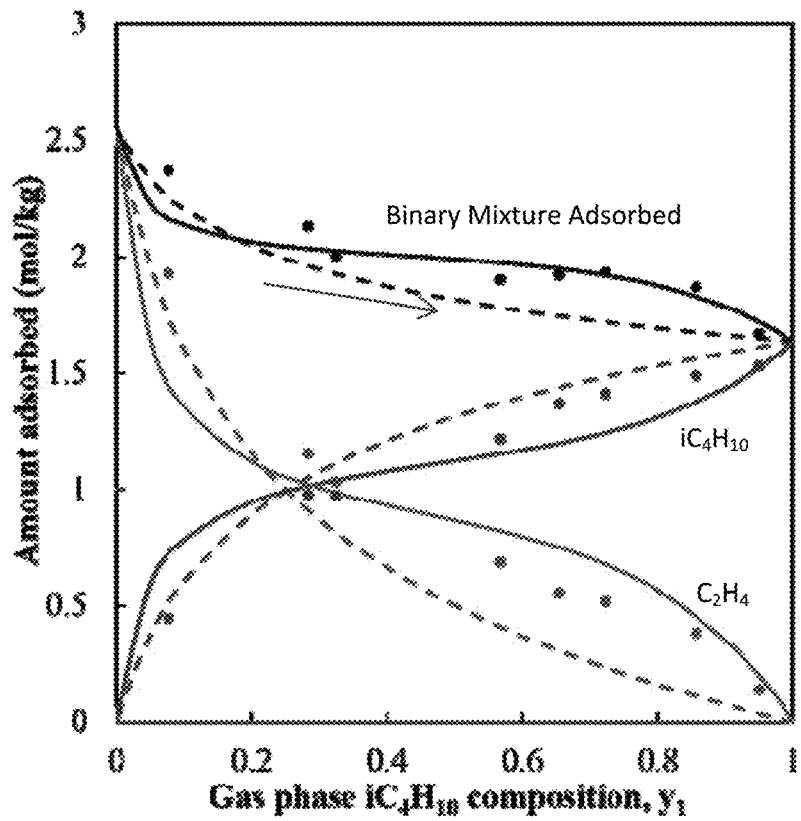
Figure 11A:
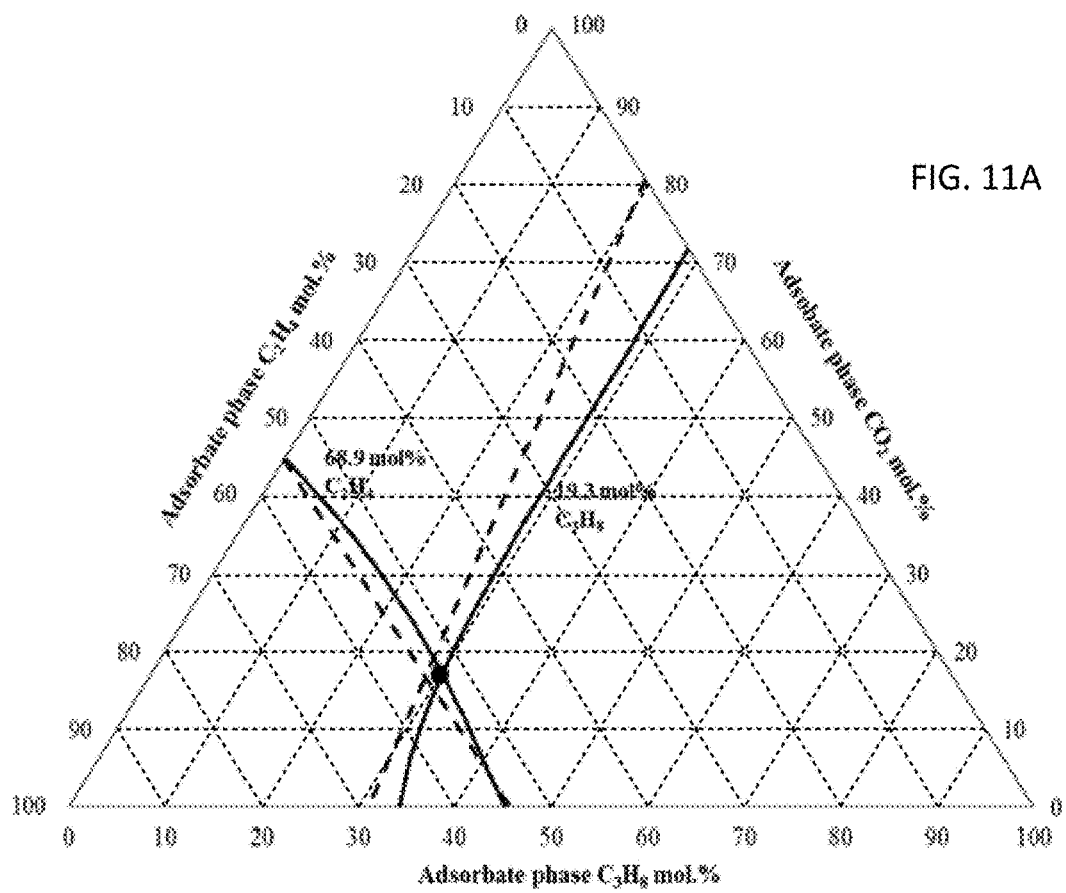
Figure 11B:
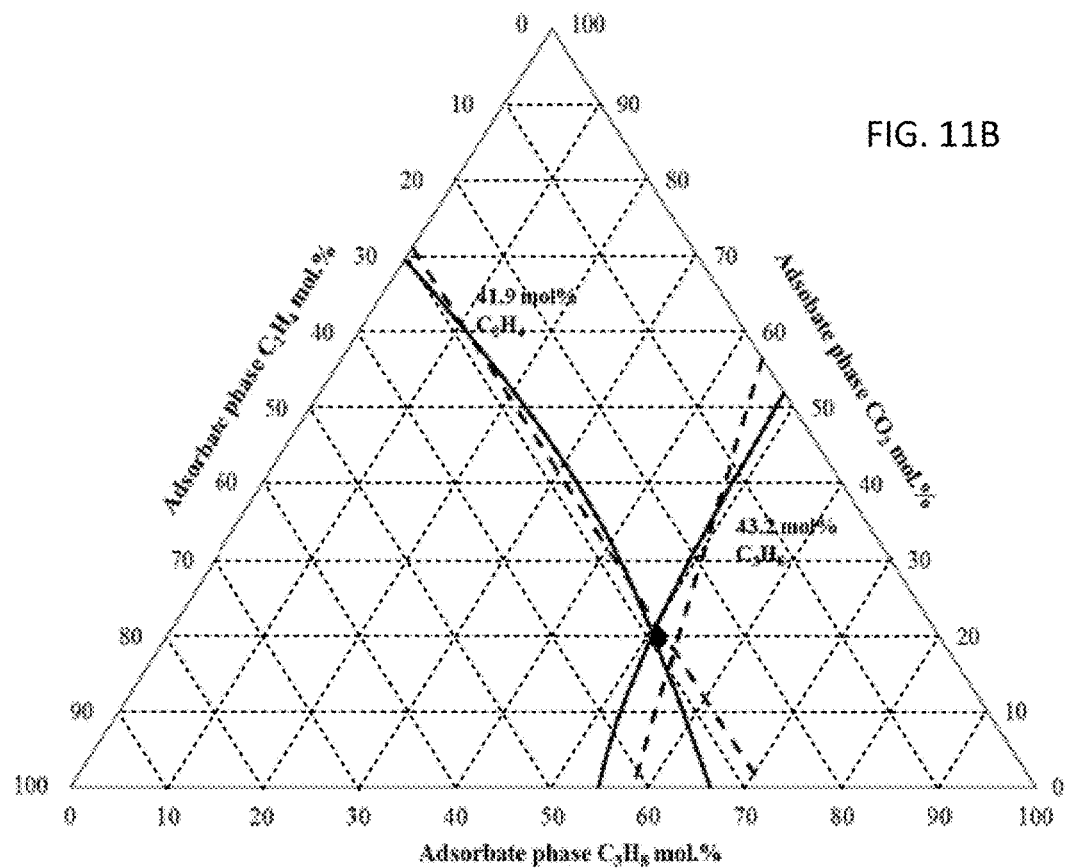
Figure 11C:
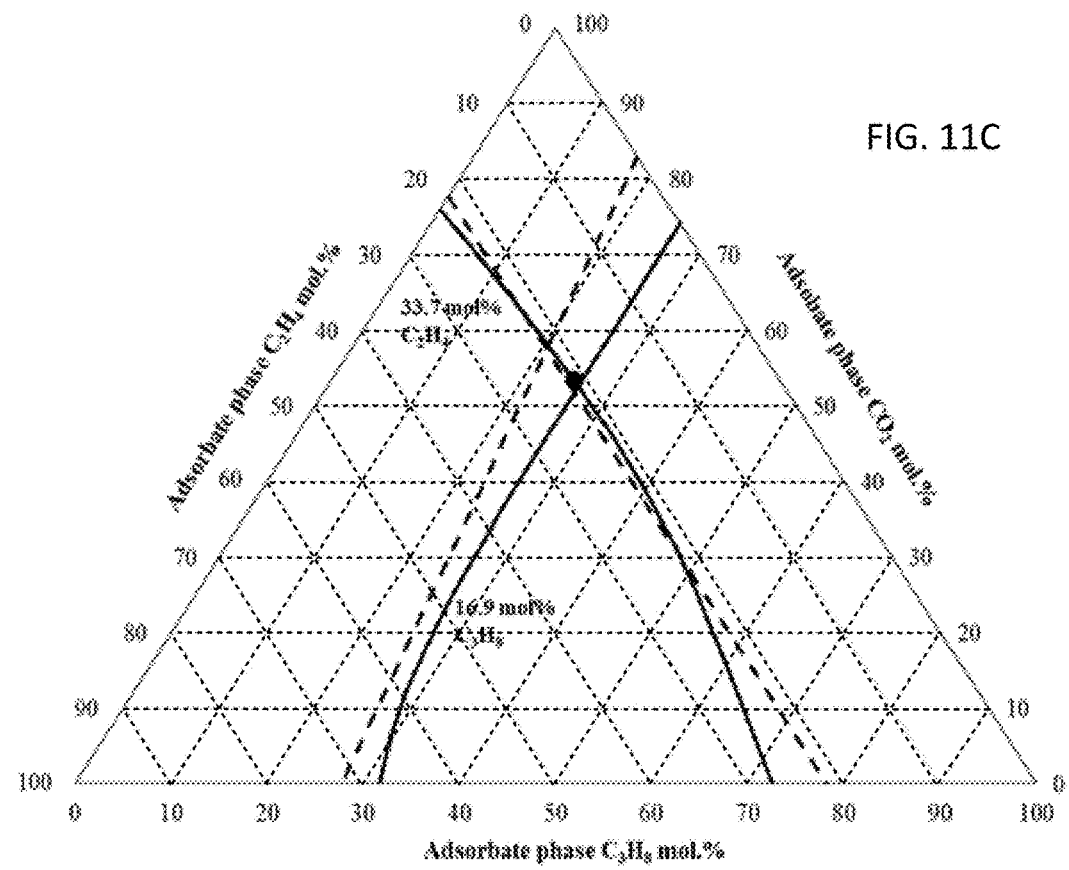
Figure 11D:
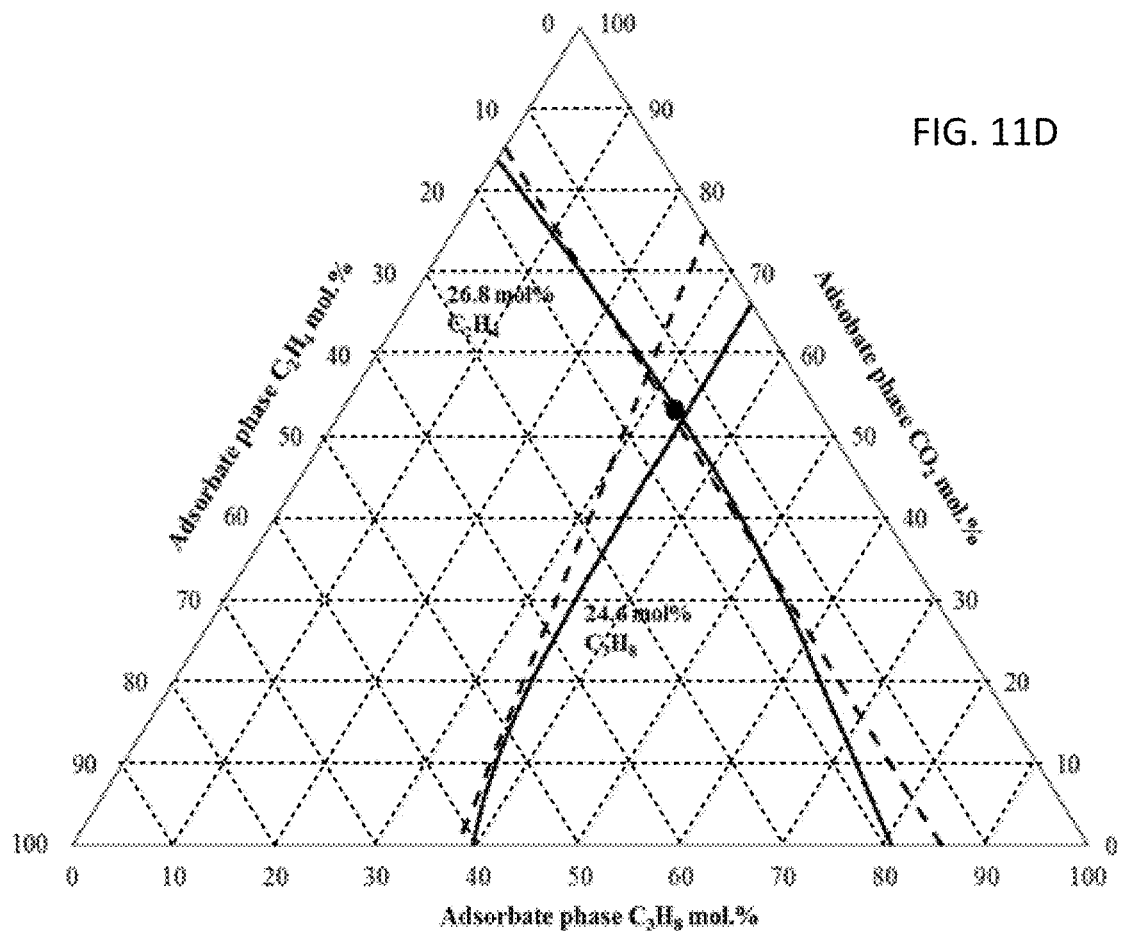

FIG. 10C is a graph comparing experimental measurement of amount adsorbed [35] for $iC_4H_{10}$(1), $C_2H_4$ (2) and total amount of the binary mixture adsorbed on zeolite 13X at 323 K and 137.8 kPa with IAST and RAST results.

FIGS. 11A, 11B, 11C, and 11D are graphs showing the adsorbate phase composition predictions of the ternary system $C_2H_4$(1)-$C_3H_8$(2)-$CO_2$(3) at 293 K and 53.3 kPa on zeolite 13X using the binary interaction parameters for the three binaries $C_2H_4(1)$-$C_3H_8(2)$, $C_2H_4(1)$-$CO_2(2)$ and $C_3H_8(1)$-$CO_2(2)$.

Figure 12:
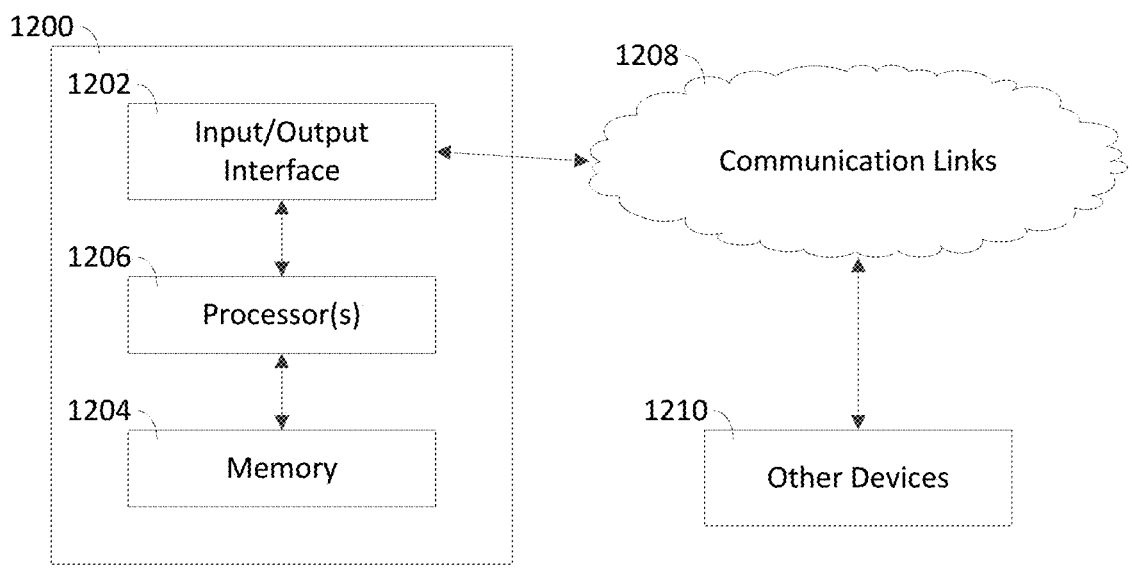

FIG. 12 is a block diagram of a system in accordance with one embodiment of the present invention.

FIG. 13 is a flowchart of a method in accordance with one embodiment of the present invention.

DETAILED DESCRIPTION OF THE INVENTION

Illustrative embodiments of the system of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Taking into consideration the adsorbate-adsorbent interactions, a novel activity coefficient model is derived from the non-random two-liquid theory for mixed-gas adsorption equilibrium. In contrast with the conventional activity coefficient models developed for bulk liquids, the new model correctly predicts negative deviations from ideality for adsorbed gas mixtures and azeotropic behavior exhibited by selected gas-adsorbent systems. Requiring a single binary interaction parameter per adsorbate-adsorbate pair, the model successfully correlates wide varieties of gas adsorption isotherm data and it is a powerful engineering thermodynamic tool in correlating and predicting multicomponent adsorption isotherms.

A novel activity coefficient model for mixed gas adsorption equilibria is described herein. The model accurately correlates binary mixture adsorption isotherm data for wide varieties of adsorbents including, but not limited to, silica gel, activated carbon, and zeolites. This model is believed to be the first and only activity coefficient model that is capable of fully representing the non-ideality of gas adsorption systems including those exhibiting azeotrope behavior. Requiring only a single binary interaction parameter per adsorbate-adsorbate binary, the model should be a very powerful engineering thermodynamic tool to correlate and predict gas adsorption equilibria in support of rigorous process modeling and simulation of multicomponent adsorption systems and processes. While this discussion focuses on the model formulation and its capability to correlate binary adsorption isotherm data, the model can be applied to correlate pure component isotherms, estimation of the binary interaction parameters from pure component isotherms, estimation of enthalpy of adsorption, and development of methodology to predict the binary interaction parameters from molecular simulations.

Figure 1:
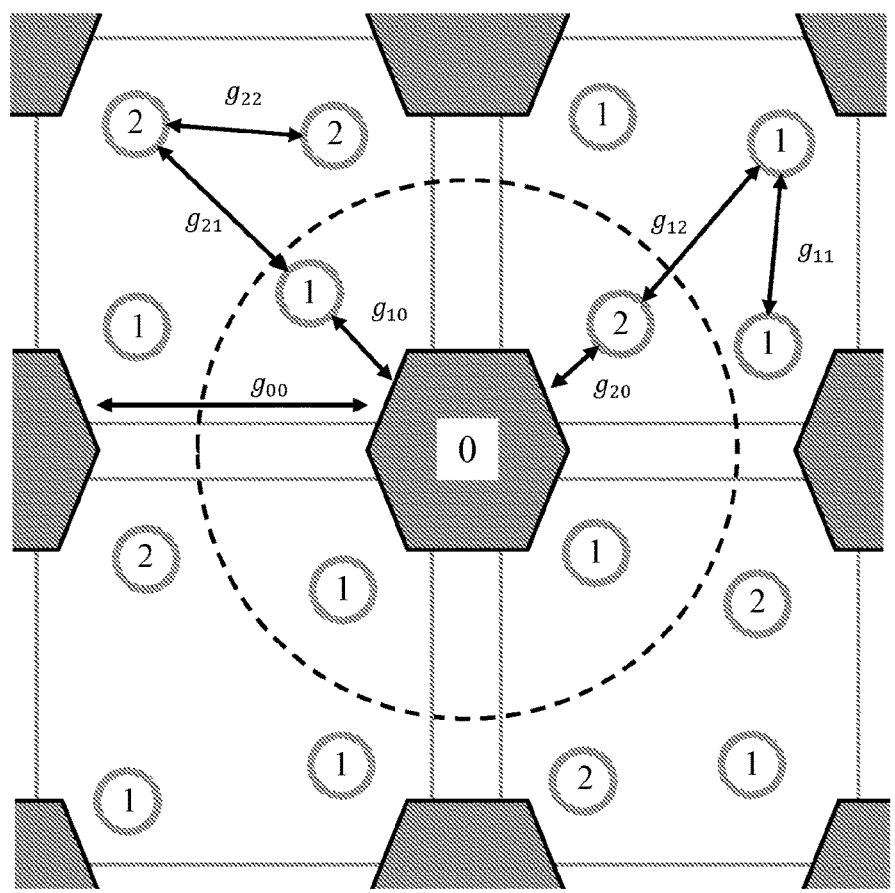
FIG. 1 illustrates a schematic representation of the adsorbent cage structure and various types of interactions occurring between adsorbate-adsorbent molecules.

The thermodynamic framework for the new activity coefficient model will now be described. Following the NRTL theory [21], the local compositions of a binary adsorbate phase are first defined. Consider that the adsorption site of adsorbent "0" is surrounded by adsorbate molecule "1" and molecule "2". This can be imagined as a situation where the adsorption site connects multiple cages in a framework with molecules adsorbed in each cage, as shown in FIG. 1, a graph showing a schematic representation of the adsorbent cage structure and various types of interactions occurring between adsorbate-adsorbent molecules. The local mole fractions of adsorbates around the adsorption site sum up to unity.

$$x_{10} + x_{20} = 1 \quad (3)$$

where $x_{10}$ and $x_{20}$ are the local mole fractions of adsorbate component 1 and adsorbate component 2, respectively. The distribution of these molecules in the local domain can be expressed in terms of bulk mole fractions, $x_1$ and $x_2$, adjusted by a Boltzmann distribution type relationship, similar to the work of Renon and Prausnitz [21].

$$\frac{x_{10}}{x_{20}} = \frac{x_1 \exp\left(-\frac{\alpha_{10} g_{10}}{RT}\right)}{x_2 \exp\left(-\frac{\alpha_{20} g_{20}}{RT}\right)} \quad (4)$$

In Eq. 4, $g_{10}$ is the interaction energy between the adsorbate molecule i (i=1, 2) and the adsorption site of the adsorbent. The adsorption site is assumed not to interact energetically with its neighboring adsorption site, therefore Eq. 4 does not include any $g_{00}$ terms. A nonrandomness factor, $\alpha$, related to the inverse of the coordination number [21, 22], is introduced to scale the interaction energy between the adsorbate molecules and the adsorption site on a per adsorbate molecule basis. Furthermore, adsorbate-adsorbate intermolecular interactions are assumed to be negligible compared to the adsorbate-adsorbent interactions. The local mole fractions can be obtained by combining Eqs. 3 and 4.

$$x_{10} = \frac{x_1 \exp\left(-\frac{\alpha_{10} g_{10}}{RT}\right)}{x_1 \exp\left(-\frac{\alpha_{10} g_{10}}{RT}\right) + x_2 \exp\left(-\frac{\alpha_{20} g_{20}}{RT}\right)} \quad (5)$$

$$x_{20} = \frac{x_2 \exp\left(-\frac{\alpha_{20} g_{20}}{RT}\right)}{x_1 \exp\left(-\frac{\alpha_{10} g_{10}}{RT}\right) + x_2 \exp\left(-\frac{\alpha_{20} g_{20}}{RT}\right)} \quad (6)$$

Once again following the derivation of Renon and Prausnitz [21], the molar excess Gibbs free energy of the adsorbate mixture is treated with Scott's two-liquid theory [23]. The molar excess free energy is the sum of the changes in residual Gibbs free energy involved in exchanging molecules of a pure adsorbate phase at the same temperature and spreading pressure of the adsorbate mixture with those in the solution weighted by their bulk mole fractions.

$$h^E = x_1(g^{(0)} - g_{pure,1}^{(0)}) + x_2(g^{(0)} - g_{pure,2}^{(0)}) \quad (7)$$

where $g^{(0)} x_1 0 g_{10} + x_{20} g_{20}$, $g_{pure,1}^{(0)} = g_{10}$, and $g_{pure,2}^{(0)} = g_{20}$. Eq. 7 can therefore be rewritten as Eq. 8.

$$g^E = x_1(x_{10}g_{10} + x_{20}g_{20}) + x_2(x_{10}g_{10} + x_{20}g_{20}) - x_1 g_{10} - x_2 g_{20} \quad (8)$$

Substituting the expressions for $x_{10}$ and $x_{20}$ from Eqs. 5 and 6 into Eq. 8 and assuming the nonrandomness factors $\alpha_{10}$ and $\alpha_{20}$ are equivalent and constant ($\alpha_{10} = \alpha_{20} = \alpha$), the excess free energy is described by Eq. 9.

$$g^E = \frac{x_1 x_2 (g_{10} - g_{20}) \left[ \exp\left(\frac{-\alpha g_{10}}{RT}\right) - \exp\left(\frac{-\alpha g_{20}}{RT}\right) \right]}{x_1 \exp\left(\frac{-\alpha g_{10}}{RT}\right) + x_2 \exp\left(\frac{-\alpha g_{20}}{RT}\right)} \quad (9)$$

In keeping with the nomenclature of NRTL, Eq. 9 can be recast as Eq. 10 using the relations $$\tau_{ij} = -\tau_{ji} = \frac{(g_{i0} - g_{j0})}{RT}, \text{ and } G_{ij} = \exp(-\alpha \tau_{ij}). \quad (10)$$

$$\frac{g^E}{RT} = \frac{x_1 x_2 \tau_{12}[G_{12} - 1]}{x_1 G_{12} + x_2}$$

The activity coefficient of adsorbate component 1 in a binary mixture is related to the partial molar excess Gibbs free energy by Eq. 11.

$$RT \ln \gamma_1 = \left[ \frac{\partial n_T g^E}{\partial n_1} \right]_{T,P,n_2} \quad (11)$$

Substituting Eq. 10 in Eq. 11 yields expressions for the activity coefficients of adsorbate component 1 and adsorbate component 2.

$$\ln \gamma_1 = \frac{x_2^2 \tau_{12}[G_{12} - 1]}{[x_1 G_{12} + x_2]^2} \quad (12)$$

$$\ln \gamma_2 = \frac{x_1^2 \tau_{21}[G_{21} - 1]}{[x_1 + x_2 G_{21}]^2} \quad (13)$$

Eqs. 12 and 13 represent the new activity coefficient expressions for the components in a binary mixture of the adsorbate phase, referred to as the adsorption Non-Random Two-Liquid equation (aNRTL). According to Eqs. 12 and 13, there are two adjustable parameters: $\alpha$ and $\tau_{12}$. Following the NRTL model convention, $\alpha$ is often fixed semi-empirically at 0.2 or 0.3 [21, 22] while $\tau_{12}$ is to be regressed from literature mixture isotherm data and reflects the difference between the adsorbate-adsorbent interactions. Since $g_{10}$ and $g_{20}$ represent the attractive interaction energy involved in adsorption, both values are negative. If $\tau_{12} < 0$, then the $g_{10}$ interaction is stronger (more negative) compared to $g_{20}$, implying that component 1 is the thermodynamically preferred adsorbate. Conversely, if $\tau_{12} > 0$, then $g_{20}$ interaction is stronger and component 2 would be the thermodynamically preferred adsorbate. Furthermore, $\tau_{12} = 0$ yields unity activity coefficients and the corresponding adsorbate phase behaves as an ideal solution described by IAST.

As mentioned earlier, it is assumed that the competitive adsorption is solely dependent on the difference between the adsorbate-adsorbent interaction, $\tau_{12}$. No assumptions are made on the spreading pressure dependence, if any, of $\tau_{12}$. Using the aNRTL model on pure component isotherms, it was found that $g_{10}$ and $g_{20}$ are a function of temperature and independent of adsorption coverage extent and spreading pressure, suggesting $\tau_{12}$ should be independent of spreading pressure.

It is interesting that the numerator of Eq. 10, the excess Gibbs energy expression derived from the NRTL theory for a binary adsorbate mixture, is consistent with the excess Gibbs energy expression proposed by Siperstein and Myers [24]. Considered the simplest form with the built-in limits required of adsorption theory, the empirical excess function of Siperstein and Myers requires up to three adjustable parameters while the proposed aNRTL model requires only one adjustable binary interaction parameter $\tau_{12}$. Given proper force field parameters for the adsorbate-adsorbent interaction, it should be possible to estimate $\tau_{12}$ from molecular sizes and potentials of mean force from molecular simulations [22].

For a multicomponent system with 'm' number of components, the molar excess Gibbs free energy can be described by Eq. 14.

$$\frac{g^E}{RT} = \sum_{i=1}^{m} x_i \frac{\sum_{j=1}^{m} x_j \tau_{ij}}{\sum_{k=1}^{m} x_k G_{ki}} \quad (14)$$

The activity coefficients are then given by Eq. 15.

$$\ln \gamma_i = \sum_{j=1}^{m} \frac{x_j^2 \tau_{ij}[G_{ij} - 1]}{[\sum_{k=1}^{m} x_k G_{kj}]^2} \quad (15)$$

To predict the activity coefficients in multicomponent systems, Eq. 15 requires only the binary interaction parameters $\tau_{ij}$ determined from binary adsorption isotherm data.

Figure 2:
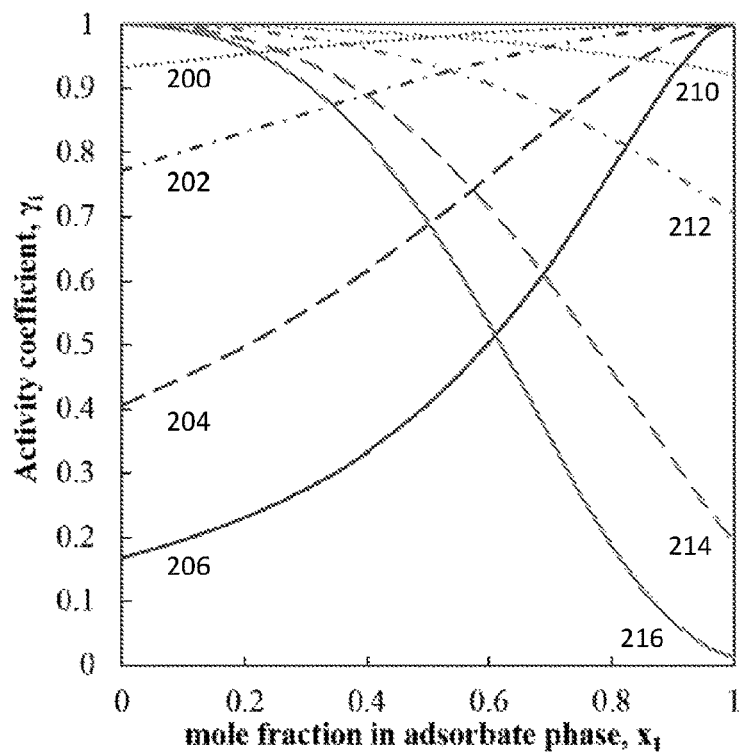
FIG. 2 illustrates the sensitivity of the calculated activity coefficients with respect to different values of $\tau_{12}$ and $\alpha=0.3$.

The sensitivity analysis of the activity coefficient model will now be described. The behavior of the proposed aNRTL activity coefficient model depends strongly on the adsorbate-adsorbent interaction energy, $\tau_{12}$. FIG. 2 is a graph illustrating the sensitivity of the calculated activity coefficients $\gamma_1$ (blue lines 200, 202, 204, 206) and $\gamma_2$ (red lines 210, 212, 214, 216) with respect to different values of $\tau_{12}$ and $\alpha = 0.3$. Activity coefficients, $\gamma_i$, are unity when $\tau_{12}$ is set to zero. The calculated activity coefficients are all less than one and span a larger range as $\tau_{12}$ moves away from zero, or the difference between the adsorbate-adsorbent interactions increases. This observed trend of activity coefficients exhibited by the model is qualitatively consistent with that reported by Myers at constant pressure. [14] The nonrandomness factor, $\alpha$, is fixed at 0.3 for the calculations shown in FIG. 2, in which $\tau_{12} = 0.5$ (dotted lines 200, 210), $\tau_{12} = 1$ (dotted dashed lines 202, 212), $\tau_{12} = 2$ (dashed lines 204, 214) and $\tau_{12} = 3$ (solid lines 206, 216). Changing the value of $\alpha$ will alter the calculated activity coefficients but the overall qualitative trends remain the same.

Implementation of the aNRTL model in VAE calculations involves first fitting pure component isotherm data to obtain a relationship between the adsorption amount and the gas phase pressure. Once the pure component isotherms are available, the spreading pressure of each component can be calculated using the Gibbs definition of adsorption, under the condition that the total area available for adsorption (A) is temperature invariant.

$$\pi_i(P_i^0) = \frac{RT}{A} \int_0^{P_i^0} n_i(P) d\ln P \qquad (16)$$

The adsorption isotherm for a pure component i can be expressed using various pure component isotherm equations such as Langmuir, Freundlich, Sips, Toth, etc. In this discussion, either the Langmuir or Sips isotherm equations are used to represent the pure component isotherm data. The Langmuir isotherm equation is given by Eq. 17, while the Sips (Langmuir-Freundlich) isotherm is given by Eq. 18.

$$n_i(P) = \frac{n_i^0 bP}{(1+bP)} \qquad (17)$$

$$n_i(P) = \frac{n_i^0 (bP)^{\frac{1}{k}}}{\left(1+(bP)^{\frac{1}{k}}\right)} \qquad (18)$$

In Eqs. 17 and 18, $n_i^0$ is the maximum amount adsorbed corresponding to a complete monolayer coverage in the Langmuir model, expressed in moles per kilogram of adsorbent; b is the Langmuir adsorption constant; k is a dimensionless empirical "heterogeneity" parameter [25]. Table 1 gives the regressed values of the Langmuir and Sips isotherm parameters for a few gas adsorption systems.

TABLE 1

Regressed values of pure component isotherm parameters on silica gel

| Binary system | Temperature (K) | Component | Isotherm type | Parameters[a] | Data Source |
|---|---|---|---|---|---|
| $O_2(1)$—$CO(2)$ | 273 | $O_2$ | Langmuir | $n^o$ = 17.20<br>b = 0.00077 | Markham and Benton[31] |
| | | CO | | $n^o$ = 14.573<br>b = 0.00174 | |
| $O_2(1)$—$CO(2)$ | 373 | $O_2$ | Langmuir | $n^o$ = 5.968<br>b = 0.00039 | |
| | | CO | | $n^o$ = 3.169<br>b = 0.001147 | |
| $O_2(1)$—$CO_2(2)$ | 373 | $O_2$ | Langmuir | $n^o$ = 14.581<br>b = 0.000165 | |
| | | $CO_2$ | | $n^o$ = 19.585<br>b = 0.002257 | |
| $CO(1)$—$CO_2(2)$ | 373 | CO | Langmuir | $n^o$ = 3.169<br>b = 0.001147 | |
| | | $CO_2$ | | $n^o$ = 19.585<br>b = 0.002257 | |
| $C_2H_2(1)$—$C_2H_4(2)$ | 298 | $C_2H_2$ | Sips | $n^o$ = 5.473<br>b = 0.0034<br>k = 1.485 | Lewis et al.[29] |
| | | $C_2H_4$ | | $n^o$ = 2.295<br>b = 0.0068<br>k = 1.056 | |
| $C_3H_6(1)$—$C_2H_4(2)$ | 273 | $C_3H_6$ | Sips | $n^o$ = 5.112<br>b = 0.0205<br>k = 1.484 | Lewis et al.[30] |
| | | $C_2H_4$ | | $n^o$ = 2.358<br>b = 0.0192<br>k = 1.0707 | |
| $C_3H_6(1)$—$C_2H_4(2)$ | 298 | $C_3H_6$ | Sips | $n^o$ = 4.585<br>b = 0.0089<br>k = 1.408 | Lewis et al.[28] |
| | | $C_2H_4$ | | $n^o$ = 2.295<br>b = 0.0068<br>k = 1.057 | Lewis et al.[29] |
| $C_3H_6(1)$—$C_2H_4(2)$ | 313 | $C_3H_6$ | Sips | $n^o$ = 5.733<br>b = 0.0027<br>k = 1.632 | Lewis et al.[30] |
| | | $C_2H_4$ | | $n^o$ = 3.423<br>b = 0.002<br>k = 1.202 | |
| $C_3H_8(1)$—$C_2H_4(2)$ | 273 | $C_3H_8$ | Sips | $n^o$ = 7.998<br>b = 0.0035<br>k = 1.376 | Lewis et al.[30] |
| | | $C_2H_4$ | | $n^o$ = 2.358<br>b = 0.0192<br>k = 1.0707 | |
| $C_3H_8(1)$—$C_2H_4(2)$ | 298 | $C_3H_8$ | Sips | $n^o$ = 11.045<br>b = 0.0009<br>k = 1.331 | Lewis et al.[28] |
| | | $C_2H_4$ | | $n^o$ = 2.295<br>b = 0.0069<br>k = 1.0566 | Lewis et al.[29] |

TABLE 1-continued

Regressed values of pure component isotherm parameters on silica gel

| Binary system | Temperature (K) | Component | Isotherm type | Parameters[a] | Data Source |
|---|---|---|---|---|---|
| $C_3H_8(1)$—$C_2H_4(2)$ | 313 | $C_3H_8$ | Sips | $n^o$ = 6.159<br>b = 0.0016<br>k = 1.215 | Lewis et al.[30] |
| | | $C_2H_4$ | | $n^o$ = 3.423<br>b = 0.002<br>k = 1.2018 | |
| $C_3H_6(1)$—$C_3H_8(2)$ | 298 | $C_3H_6$ | Sips | $n^o$ = 4.585<br>b = 0.0089<br>k = 1.409 | Lewis et al.[28] |
| | | $C_3H_8$ | | $n^o$ = 11.045<br>b = 0.0009<br>k = 1.331 | |

[a]Units of $n^o$ and b are (mol/kg) and (kPa$^{-1}$) respectively.

Generally speaking, the Langmuir isotherm is the model of choice since it involves only two adjustable parameters. The Sips isotherm is used when the Langmuir isotherm does not adequately correlate the isotherm data.

Figure 3:
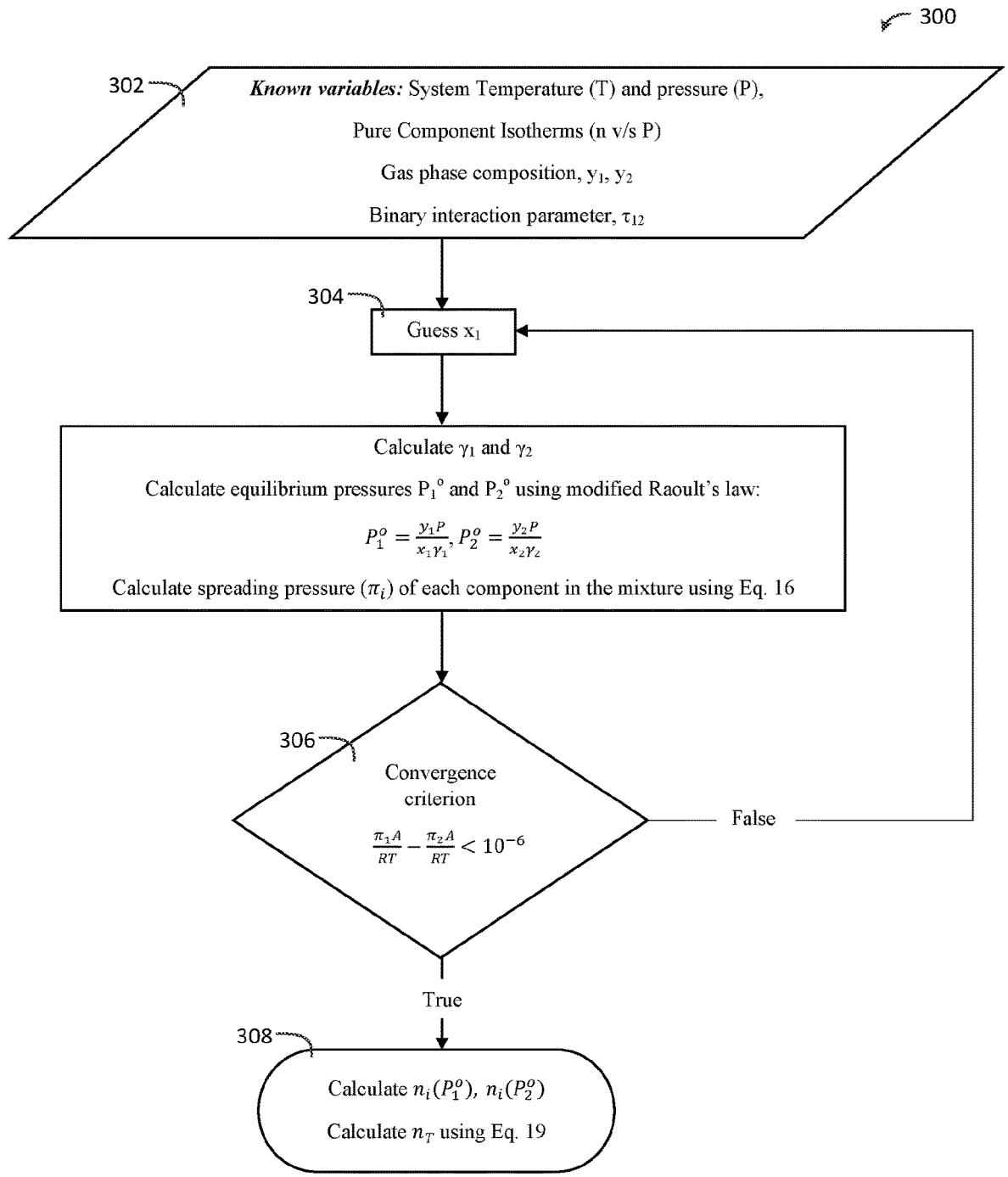
FIG. 3 shows an algorithm for calculating adsorbate phase composition, $x_i$, and adsorption amount, $n_T$, given system temperature (T) and pressure (P), gas phase composition, $y_i$, and binary interaction parameter, $\tau_{12}$.

If $\tau_{ij}$'s are known, then the remaining RAST calculations are straight forward. Shown in FIG. 3 is an algorithm 300 for calculating adsorbate phase composition, $x_i$, and adsorption amount, $n_T$, given system temperature (T) and pressure (P), gas phase composition, $y_i$, and binary interaction parameter, $\tau_{12}$. The calculation algorithm for a binary gas adsorption system starts with an assumed $x_1$ ($x_2=1-x_1$), then followed by the activity coefficient calculations with Eqs. 12 and 13. Equilibrium pressure $P_i^o$ and spreading pressure $\pi_i$ of each component are then calculated with Eqs. 2 and 16 respectively. The value for $x_1$ is iterated and considered converged when the equality of the component spreading pressures is satisfied. The total number of adsorbed molecules is then calculated with Eq. 19.

$$\frac{1}{n_T} = \sum_i \frac{x_i}{n_i(P_i^o)} \quad (19)$$

The procedures described in FIG. 3 can be easily extended to multicomponent systems.

More specifically, the known variables are provided in block 302, namely: system temperature (T) and pressure (P); pure component isotherms (n v/s P); gas phase composition, $y_1$, $y_2$; and binary interaction parameter, $\tau_{12}$. A guess of $x_1$ is provided in block 304. In block 306, $\gamma_1$ and $\gamma_2$ are calculated, equilibrium pressures $P_1^o$ and $P_2^o$ are calculated using modified Raoult's law:

$$P_1^o = \frac{y_1 P}{x_1 \gamma_1}, \quad P_2^o = \frac{y_2 P}{x_2 \gamma_2};$$

and the spreading pressure $\pi_i$ of each component in the mixture is calculated using Eq. 16. If the convergence criterion, $$\frac{\pi_1 A}{RT} - \frac{\pi_2 A}{RT} < 10^{-6},$$

is false, as determined in decision block 308, the process loops back to block 304 to guess the next $x_1$. If however, the convergence criterion is true, as determined in decision block 308, $n_i(P_1^o)$, $n_i(P_2^o)$ are calculated, and $n_T$ is calculated using Eq. 19 in block 310.

Figure 4:
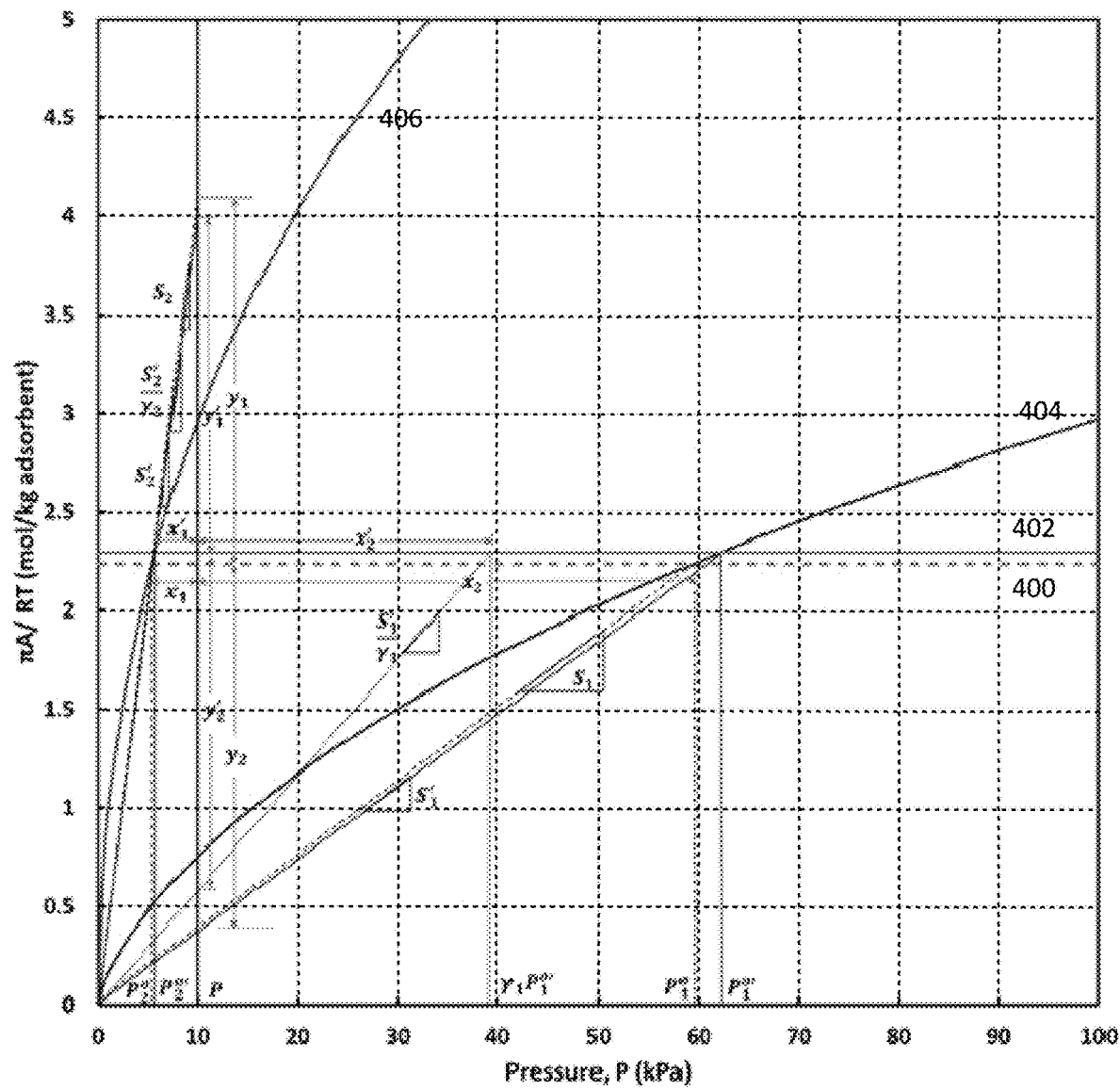
FIG. 4 is a graph showing a schematic representation of the spreading pressure calculation in the ideal case $$\left(\frac{\pi A}{RT}\right)_{IAST}$$

FIG. 4 is a graph illustrating the equality of the component spreading pressures when the activity coefficients are considered. More specifically, FIG. 4 is a graph showing a schematic representation of the spreading pressure calculation in the ideal case $$\left(\frac{\pi A}{RT}\right)_{IAST}$$

(green dashed line 400) and the real case scenario $$\left(\frac{\pi A}{RT}\right)_{RAST}$$

(green solid line 402) for an equimolar $C_2H_6$ (1, blue solid line 404) —$C_3H_6$ (2, red solid line 406) mixture from the pure component isotherms on activated carbon [26] at 323 K and 10 kPa, $\tau_{12}$=1.515. The adsorption of an equimolar $C_2H_6$-$C_3H_6$ [16] mixture on activated carbon at 323 K and 10 kPa has been shown with both the IAST assumption and the RAST assumption. In the IAST scenario, $\gamma_i$=1, the spreading pressure of equimolar composition of $C_2H_6$—$C_3H_6$ mixture [26] on activated carbon would have the equilibrium pressures corresponding to $P_1^o$ and $P_2^o$. For example, with $y_1=y_2=0.5$, the equilibrium partial pressures are $P_1^o$=59.45 kPa and $P_2^o$=5.46 kPa and the corresponding spreading pressure of the mixture is $$\left(\frac{\pi A}{RT}\right)_{IAST} = 2.238 \frac{\text{mol}}{\text{kg adsorbent}}.$$

The adsorbate phase compositions of the mixture corresponding to the above calculated spreading pressure would be $x_1$=0.084 and $x_2$=0.916. However, when the activity coefficients are taken into consideration as in the RAST scenario, the spreading pressure of the mixture is corresponding to the equilibrium pressures of $P_1^{o'}$ and $P_2^{o'}$. Thus, for $y_1=y_2=0.5$, the corresponding equilibrium partial pressures would be $P_1^{o'}=62.23$ kPa and $P_2^{o'}=5.77$ kPa as shown in FIG. 4 and the spreading pressure of the mixture would be $$\left(\frac{\pi A}{RT}\right)_{RAST} = 2.296 \frac{\text{mol}}{\text{kg adsorbent}}$$

which would yield adsorbate phase compositions of $x'_1=0.128$ and $x'_2 32\ 0.872$.

Binary adsorption behavior was studied on different adsorbents including activated carbon, silica gel and various types of zeolite molecular sieves. The surface of activated carbon and silica gels is nonpolar or slightly polar and their heat of adsorption is generally low [27]. Therefore, these adsorbents are typically used for adsorbing nonpolar or weakly polar organic molecules or molecules having similar size and shape characteristics. As a result, IAST model tends to give satisfactory predictions for gas mixtures adsorbed on silica gel and activated carbon. Zeolites on the other hand are highly non-ideal, polar adsorbents and therefore, based on their shape and aperture size, they have wide applications such as air purification, air separation, separations based on molecular size and shape etc. [27] IAST does not give accurate predictions for adsorption with zeolites.

Tables 1 to 6 present the values of the pure component adsorption isotherm parameters and the binary interaction parameters obtained from data regression of pure component isotherm data and binary mixture adsorption data available in the literature. The objective function used in the regression of the binary mixture adsorption data is to minimize the average absolute deviation (AAD %) which is defined as:

$$AAD\ \% = \frac{100}{N} \sum_{j=1}^{N} \left| \frac{x_{1,j}^{calc} - x_{1,j}^{exp}}{x_{1,j}^{exp}} \right| \quad (20)$$

where $x_1^{calc}$ and $x_1^{exp}$ are the calculated value and the experimental value of the mole fraction of component 1 in the adsorbate phase respectively, and N is the total number of data points in the binary mixture adsorption data set. The AAD's have been reported for the calculations performed using the new activity coefficient model and the IAST model.

Silica Gel

Table 1 presents the pure component adsorption isotherm parameters of various systems [28-31] obtained using either Langmuir or Sips equation whereas Table 2 presents the binary interaction parameters regressed using the mixture isotherm data of the above systems.

TABLE 2

Regressed values of binary interaction parameter on silica gel

| Binary System | Temperature (K) | $\tau_{12}{}^a$ | No. of data points | AAD % (Present invention) | AAD % (IAST) | Data Source |
|---|---|---|---|---|---|---|
| $O_2(1)$—$CO(2)$ | 273 | 0.406 | 3 | 0.87 | 1.84 | Markhom |
| | 373 | 1.006 | 4 | 1.39 | 6.83 | and |
| $O_2(1)$—$CO_2(2)$ | 373 | 0.305 | 5 | 17.26 | 18.43 | Benton[31] |
| $CO(1)$—$CO_2(2)$ | 373 | 1.256 | 5 | 16.35 | 33.49 | |
| $C_2H_2(1)$—$C_2H_4(2)$ | 298 | 0 | 6 | 26.31 | 26.31 | Lewis et al.[29] |
| $C_3H_6(1)$—$C_2H_4(2)$ | 273 | −0.819 | 12 | 6.55 | 7.43 | Lewis et al.[30] |
| | 298 | 0 | 6 | 1.46 | 1.46 | |
| | 313 | 0 | 6 | 10.96 | 10.96 | |
| $C_3H_8(1)$—$C_2H_4(2)$ | 273 | −0.452 | 12 | 3.95 | 3.97 | |
| | 298 | 0 | 9 | 5.87 | 5.87 | |
| | 313 | 0 | 6 | 1.99 | 1.99 | |
| $C_3H_6(1)$—$C_3H_8(2)$ | 298 | −0.817 | 12 (7) | 6.19 | 6.49 | Lewis et al.[28] |

$^a\alpha = 0.3$, Numbers in the brackets represent the actual number of data points used in the regression The regressed $\tau_{12}$ values are generally close to zero, suggesting relatively ideal adsorbate phase. Therefore, the RAST results are only slightly better than the IAST results. As an example, FIGS. 5A and 5B are graphs comparing the experimental isotherm data and the experimental amount adsorbed [31] respectively for $CO(1)$-$CO_2(2)$ binary mixture at 373 K and 101.3 kPa with the IAST and the RAST results. FIG. 5A is a graph showing a comparison of experimental equilibrium data [31] of adsorbed CO(1, dots)-$CO_2$ (2) binary mixture on silica gel at 373 K and 101.325 kPa with IAST (dashed line) and RAST (solid line) results. FIG. 5B is a graph showing a comparison of experimental measurement of amount adsorbed [31] for CO (1, blue dots), $CO_2$ (2, red dots) and total amount of the binary mixture adsorbed (black dots) on silica gel at 373 K and 101.325 kPa with IAST (dashed line) and RAST (solid line) results. It can be observed that, with $\tau_{12}=1.256$, the aNRTL model is able to capture the non-ideality of the mixture by accurately predicting the mole fraction in the adsorbate phase and the total amount adsorbed.

Activated Carbon

Tables 3 and 4 enlist the pure component isotherm parameters and the binary interaction parameters regressed using the pure component and mixture adsorption isotherm data [26, 28-30] respectively.

TABLE 3

Regressed values of pure component isotherm parameters on activated carbon

| Binary system | Temperature (K) | Component | Isotherm type | Parameters | Data Source |
|---|---|---|---|---|---|
| $C_2H_2(1)$—$C_2H_4(2)$ | 298 | $C_2H_2$ | Sips | $n^o$ = 5.963<br>b = 0.0038<br>k = 1.458 | Lewis et al.[29] |
| | | $C_2H_4$ | | $n^o$ = 3.522<br>b = 0.0163<br>k = 1.263 | |
| $C_3H_6(1)$—$C_3H_8(2)$ | 298 | $C_3H_6$ | Sips | $n^o$ = 3.713<br>b = 0.0452<br>k = 1.494 | Lewis et al.[30] |
| | | $C_3H_8$ | | $n^o$ = 5.478<br>b = 0.0076<br>k = 2.333 | |
| $CH_4(1)$—$C_2H_4(2)$ | 323 | $CH_4$ | Langmuir | $n^o$ = 1.432<br>b = 0.0040 | Costa et al.[26] |
| | | $C_2H_4$ | Sips | $n^o$ = 3.281<br>b = 0.0082<br>k = 1.331 | |
| $CH_4(1)$—$C_2H_6(2)$ | 323 | $CH_4$ | Langmuir | $n^o$ = 1.432<br>b = 0.0040 | |
| | | $C_2H_6$ | Sips | $n^o$ = 3.429<br>b = 0.0077<br>k = 1.429 | |
| $C_2H_4(1)$—$C_2H_6(2)$ | 323 | $C_2H_4$ | Sips | $n^o$ = 3.281<br>b = 0.0082<br>k = 1.331 | |
| | | $C_2H_6$ | | $n^o$ = 3.429<br>b = 0.0077<br>k = 1.429 | |
| $C_2H_4(1)$—$C_3H_6(2)$ | 323 | $C_2H_4$ | Sips | $n^o$ = 3.281<br>b = 0.0082<br>k = 1.331 | |
| | | $C_3H_6$ | | $n^o$ = 6.702<br>b = 0.0065<br>k = 1.974 | |
| $C_2H_6(1)$—$C_3H_6(2)$ | 323 | $C_2H_6$ | Sips | $n^o$ = 3.429<br>b = 0.0077<br>k = 1.429 | |
| | | $C_3H_6$ | | $n^o$ = 6.702<br>b = 0.0065<br>k = 1.974 | |

TABLE 4

Regressed values of binary interaction parameter on activated carbon

| Binary System | Temperature (K) | $\tau_{12}$ | No. of data points | AAD % (Present invention) | AAD % (IAST) | Data Source |
|---|---|---|---|---|---|---|
| $C_2H_2(1)$—$C_2H_4(2)$ | 298 | 0 | 10 | 10.36 | 10.36 | Lewis et al.[29] |
| $C_3H_6(1)$—$C_3H_8(2)$ | 298 | −0.779 | 18 | 15.81 | 19.03 | Lewis et al.[28] |
| $CH_4(1)$—$C_2H_4(2)$ | 323 | 0.568 | 5 | 3.51 | 6.35 | Costa et al.[26] |
| $CH_4(1)$—$C_2H_6(2)$ | 323 | 0 | 6 | 12.26 | 12.26 | |
| $C_2H_4(1)$—$C_2H_6(2)$ | 323 | 0 | 5 | 5.26 | 5.26 | |
| $C_2H_4(1)$—$C_3H_6(2)$ | 323 | 0.831 | 7 | 3.40 | 7.95 | |
| $C_2H_6(1)$—$C_3H_6(2)$ | 323 | 1.515 | 8 | 5.45 | 20.50 | |

Similar to the silica gel cases above, the regressed $\tau_{12}$ values are close to zero, suggesting relatively ideal adsorbate phase. Therefore, the RAST results are only slightly better than the IAST predictions. FIGS. 6A and 6B are graphs showing the model results for the adsorbate phase composition and the amount adsorbed respectively for $C_2H_6(1)$-$C_3H_6(2)$ binary mixture [26] on activated carbon at 323 K and 10 kPa. The RAST model results, with $\tau_{12}$=1.515, are much better than the IAST results for this binary. FIG. 6A is a graph showing a comparison of experimental equilibrium data [26] of adsorbed $C_2H_6$(1, dots)-$C_3H_6$ (2) binary mixture on activated carbon at 323 K and 10 kPa with IAST (dashed line) and RAST (solid line) results. FIG. 6B is a graph showing a comparison of experimental measurement of amount adsorbed [26] for $C_2H_6$ (1, blue dots), $C_3H_6$ (2, red dots) and total amount of the binary mixture adsorbed (block dots) on activated carbon at 323 K and 10 kPa with IAST (dashed line) and RAST (solid line) results

Zeolites

Tables 5 and 6 report the pure component isotherm parameters and the binary interaction parameters respectively for various kinds of zeolites regressed using the pure component and mixture adsorption isotherm data [17, 32-36].

TABLE 5

Regressed values of pure component isotherm parameters on zeolites

| Binary system | Temperature (K) | Component | Isotherm type | Parameters | Data Source |
|---|---|---|---|---|---|
| Zeolite Molecular Sieve (ZSM)- 5A | | | | | |
| $O_2(1)$—$N_2(2)$ | 144 | $O_2$ | Sips | $n^o$ = 5.724<br>b = 0.106<br>k = 1.226 | Danner and Wenzel[32] |
| | | $N_2$ | | $n^o$ = 4.866<br>b = 1.278<br>k = 1.728 | |
| $CO_2(1)$—$C_2H_4(2)$ | 293 | $CO_2$ | Sips | $n^o$ = 19.18<br>b = 0.00001<br>k = 2.69 | Calleja et al.[33] |
| | | $C_2H_4$ | | $n^o$ = 3.952<br>b = 0.002<br>k = 2.678 | |
| $CO_2(1)$—$C_3H_8(2)$ | | $CO_2$ | Sips | $n^o$ = 19.18<br>b = 0.00001<br>k = 2.69 | |
| | | $C_3H_8$ | | $n^o$ = 1.494<br>b = 1.361<br>k = 2.036 | |
| $C_2H_4(1)$—$C_3H_8(2)$ | | $C_2H_4$ | Sips | $n^o$ = 3.952<br>b = 0.002<br>k = 2.678 | |
| | | $C_3H_8$ | | $n^o$ = 1.494<br>b = 1.361<br>k = 2.036 | |
| Zeolite 10X | | | | | |
| $O_2(1)$—$N_2(2)$ | 144 | $O_2$ | Langmuir | $n^o$ = 6.879<br>b = 0.0263 | Danner and Wenzel[32] |
| | | $N_2$ | Sips | $n^o$ = 7.782<br>b = 0.0299<br>k = 2.46 | |
| $O_2(1)$—$N_2(2)$ | 172 | $O_2$ | Sips | $n^o$ = 29.74<br>b = 0.0003<br>k = 1.354 | Nolan et al.[34] |
| | | $N_2$ | | $n^o$ = 6.966<br>b = 0.0068<br>k = 2.106 | |
| | 227 | $O_2$ | Sips | $n^o$ = 3.267<br>b = 0.0015<br>k = 0.984 | |
| | | $N_2$ | | $n^o$ = 7.113<br>b = 0.0006<br>k = 1.677 | |
| $O_2(1)$—$CO(2)$ | 144 | $O_2$ | Langmuir | $n^o$ = 6.879<br>b = 0.0263 | Danner and Wenzel[32] |
| | | CO | Sips | $n^o$ = 7.232<br>b = 0.222<br>k = 2.5 | |
| $O_2(1)$—$CO(2)$ | 177 | $O_2$ | Sips | $n^o$ = 29.74<br>b = 0.0003<br>k = 1.354 | Nolan et al.[34] |
| | | CO | | $n^o$ = 6.162<br>b = 0.052<br>k = 2.167 | |
| | 227 | $O_2$ | Sips | $n^o$ = 3.267<br>b = 0.0015<br>k = 0.984 | |
| | | CO | | $n^o$ = 4.254<br>b = 0.0085<br>k = 1.723 | |
| Zeolite 13X | | | | | |
| $C_2H_4(1)$—$CO_2(2)$ | 298 | $C_2H_4$ | Sips | $n^o$ = 3.161<br>b = 0.183<br>k = 1.482 | Hyun and Danner[35] |

TABLE 5-continued

Regressed values of pure component isotherm parameters on zeolites

| Binary system | Temperature (K) | Component | Isotherm type | Parameters | Data Source |
|---|---|---|---|---|---|
| | | $CO_2$ | | $n^o = 4.50$<br>$b = 0.115$<br>$k = 1.35$ | |
| $iC_4H_{10}(1)$—$C_2H_4(2)$ | 298 | $iC_4H_{10}$ | Sips | $n^o = 2.0$<br>$b = 0.80$<br>$k = 1.7$ | |
| | | $C_2H_4$ | | $n^o = 3.161$<br>$b = 0.183$<br>$k = 1.482$ | |
| | 323 | $iC_4H_{10}$ | Sips | $n^o = 1.78$<br>$b = 1.35$<br>$k = 2.15$ | |
| | | $C_2H_4$ | | $n^o = 3.04$<br>$b = 0.067$<br>$k = 1.35$ | |
| | 373 | $iC_4H_{10}$ | Sips | $n^o = 1.387$<br>$b = 0.259$<br>$k = 1.003$ | |
| | | $C_2H_4$ | | $n^o = 2.643$<br>$b = 0.016$<br>$k = 1.195$ | |
| $iC_4H_{10}(1)$—$C_2H_6(2)$ | 298 | $iC_4H_{10}$ | Sips | $n^o = 2.0$<br>$b = 0.80$<br>$k = 1.7$ | |
| | | $C_2H_6$ | | $n^o = 2.678$<br>$b = 0.041$<br>$k = 0.911$ | |
| $C_2H_4(1)$—$C_3H_8(2)$ | 293 | $C_2H_4$ | Sips | $n^o = 2.246$<br>$b = 0.204$<br>$k = 1.091$ | Calleja et al.[36] |
| | | $C_3H_8$ | | $n^o = 2.246$<br>$b = 0.5802$<br>$k = 1.106$ | |
| $C_2H_4(1)$—$CO_2(2)$ | | $C_2H_4$ | Sips | $n^o = 2.246$<br>$b = 0.204$<br>$k = 1.091$ | |
| | | $CO_2$ | | $n^o = 4.741$<br>$b = 0.0873$<br>$k = 1.461$ | |
| $C_3H_8(1)$—$CO_2(2)$ | | $C_3H_8$ | Sips | $n^o = 2.246$<br>$b = 0.5802$<br>$k = 1.106$ | |
| | | $CO_2$ | | $n^o = 4.741$<br>$b = 0.0873$<br>$k = 1.461$ | |
| Zeolite H-Mordenite | | | | | |
| $CO_2(1)$—$H_2S(2)$ | 303 | $CO_2$ | Sips | $n^o = 4.761$<br>$b = 0.007$<br>$k = 2.009$ | Talu and Zwiebel[17] |
| | | $H_2S$ | | $n^o = 3.372$<br>$b = 0.184$<br>$k = 2.446$ | |
| $C_3H_8(1)$—$CO_2(2)$ | | $C_3H_8$ | Sips | $n^o = 1.150$<br>$b = 0.395$<br>$k = 1.551$ | |
| | | $CO_2$ | | $n^o = 4.761$<br>$b = 0.007$<br>$k = 2.009$ | |
| $H_2S(1)$—$C_3H_8(2)$ | | $H_2S$ | Sips | $n^o = 3.372$<br>$b = 0.184$<br>$k = 2.446$ | |
| | | $C_3H_8$ | | $n^o = 1.150$<br>$b = 0.395$<br>$k = 1.551$ | |

TABLE 6

Regressed values of binary interaction parameter on zeolites

| Binary System | Temperature (K) | $\tau_{12}$ | No. of data points | AAD % (Present invention) | AAD % (IAST) | Data Source |
|---|---|---|---|---|---|---|
| ZSM 5A | | | | | | |
| $O_2(1)$—$N_2(2)$ | 144 | 1.410 | 11 | 8.42 | 23.36 | Danner and Wenzel[32] |
| $CO_2(1)$—$C_2H_4(2)$ | 293 | 0.556 | 42 | 2.26 | 3.56 | Calleja et al.[33] |
| $CO_2(1)$—$C_3H_8(2)$ | | 2.313 | 38 | 6.58 | 38.57 | |
| $C_2H_4(1)$—$C_3H_8(2)$ | | 2.434 | 39 | 12.50 | 35.92 | |
| Zeolite 10X | | | | | | |
| $O_2(1)$—$N_2(2)$ | 144 | 1.847 | 11 | 5.16 | 30.65 | Danner and Wenzel[32] |
| $O_2(1)$—$N_2(2)$ | 172 | 1.298 | 9 | 1.81 | 15.66 | Nolan et al.[34] |
| | 227 | 1.015 | 13 | 7.06 | 11.56 | |
| $O_2(1)$—$CO(2)$ | 144 | 2.288 | 11 | 10.63 | 51.79 | Danner and Wenzel[32] |
| $O_2(1)$—$CO(2)$ | 172 | 1.513 | 16 | 3.83 | 30.19 | Nolan et al.[34] |
| | 227 | 1.276 | 14 | 21.45 | 37.38 | |
| Zeolite 13X | | | | | | |
| $C_2H_4(1)$—$CO_2(2)$ | 298 | 2.056 | 6 | 14.66 | 26.43 | Hyun and Danner[35] |
| $iC_4H_{10}(1)$—$C_2H_4(2)$ | 298 | 3.071 | 10 | 17.12 | 43.58 | |
| | 323 | 2.084 | 8 | 8.22 | 16.21 | |
| | 373 | 0.187 | 6 | 5.04 | 5.12 | |
| $iC_4H_{10}(1)$—$C_2H_6(2)$ | 298 | 0 | 10 | 11.48 | 11.48 | |
| $C_2H_4(1)$—$C_3H_8(2)$ | 293 | 1.325 | 28 | 9.56 | 19.29 | Calleja et al.[36] |
| $C_2H_4(1)$—$CO_2(2)$ | | 0.758 | 33 | 6.42 | 8.83 | |
| $C_3H_8(1)$—$CO_2(2)$ | | 1.727 | 31 | 21.06 | 27.29 | |
| Zeolite H-Mordenite | | | | | | |
| $CO_2(1)$—$H_2S(2)$ | 303 | 1.947 | 5 | 4.77 | 39.59 | Talu and Zwiebel[17] |
| $C_3H_8(1)$—$CO_2(2)$ | | 4.201 | 4 | 6.48 | 41.89 | |
| $H_2S(1)$—$C_3H_8(2)$ | | −4.094 | 5 | 9.10 | 23.29 | |

FIGS. 7A to 10C are graphs comparing the experimental data with the IAST and RAST model results for various mixtures adsorbed on the zeolites.

FIGS. 7A and 7B are graphs showing the comparison of the experimental equilibrium data and the experimental amount adsorbed [32] respectively for $O_2(1)$-$N_2(2)$ mixture on zeolite molecular sieve (ZSM)-5A at 144 K and 101.325 kPa with the IAST and the RAST model results. FIG. 7A shows a comparison of experimental equilibrium data [32] of adsorbed $O_2(1)$-$N_2(2)$ binary mixture on ZSM-5A at 144 K and 101.325 kPa with IAST (dashed line) and RAST (solid line) results. FIG. 7B shows a comparison of experimental measurement of amount adsorbed [32] for $O_2$ (1, blue dots), $N_2$ (2, red dots) and total amount of the binary mixture adsorbed (black dots) on ZSM-5A at 144 K and 101.325 kPa with IAST (dashed line) and RAST (solid line) results. The RAST results, with $\tau_{12}$=1.410, are superior to those of the IAST results.

FIG. 8A is a graph showing a comparison of the experimental equilibrium data [32, 34] for $O_2(1)$-$N_2(2)$ mixture at different temperatures and 101.325 kPa with the RAST model results on zeolite 10X. FIG. 8A shows a comparison of experimental equilibrium data of adsorbed $O_2(1)$-$N_2(2)$ binary mixture on zeolite 10X at 144 K (squares, [32]), 172 K (triangles, [35]) and 227 K (dots, [35]) and 101.325 kPa with IAST (dashed line) and RAST (solid line) results. The model gives excellent predictions and clearly depicts the effect of temperature on the value of $\tau_{12}$. It can be observed from Table 6 that the value of $\tau_{12}$ increases from 1.015 at 227 K to 1.847 at 144 K, thereby indicating that the system becomes less non-ideal with the increase in temperature. FIG. 8B is a graph showing the phenomena of drastically changing activity coefficients with increase in temperature. FIG. 8B is a graph showing the activity coefficients of adsorbed $O_2$ (blue line)-$N_2$ (red line) binary mixture on zeolite 10X at 144 K (short dashed line), 172 K (dashed line) and 227 K (solid line), and 101.325 kPa. The values of activity coefficients $\gamma_1$ and $\gamma_2$ can be as low as 0.2-0.4 as the temperature decreases to 144 K, and are in the range of 0.7 to 1 at 227 K. This explains why IAST would give poor predictions at lower temperatures as it would not be able to capture the highly negative deviations from Raoult's law. FIG. 8C illustrates the behavior of excess spreading pressure, $$\frac{\Delta \pi A}{RT},$$

which could be defined as the difference between the spreading pressure of the mixture at non-ideal conditions and the spreading pressure of the mixture at ideal conditions. This difference keeps on increasing with the decrease in temperature which reflects the fact that a mixture becomes more and more non-ideal with the decrease in temperature. FIG. 8C shows the excess spreading pressure of the adsorbed $O_2(1)$-$N_2(2)$ binary mixture on zeolite 10X at 144 K (short dashed line), 172 K (dashed line) and 227 K (solid line), and 101.325 kPa.

FIGS. 9A, 9B, and 9C are graphs showing the adsorption phenomena of $C_3H_8(1)$-$CO_2(2)$ on zeolite H-Mordenite at 303 K and 41 kPa. FIG. 9A is a graph showing the Comparison of experimental pure component adsorption isotherm data [17] of $C_3H_8$(1, blue dots) and $CO_2$(2, red dots) on zeolite H-Mordenite at 303 K with Sips isotherm correlations (solid line). Although Sips can quantitatively capture the pure component isotherm data for $CO_2$, it fails to correlate the isotherm data for $C_3H_8$. Clearly better pure component isotherm models are still required if we are going to accurately correlate and predict adsorption equilibria. Another very interesting observation is that the pure component isotherms of $C_3H_8$ and $CO_2$ cross each other at low coverage which leads to an azeotrope-forming behavior as would be seen in the binary experimental data. This crossover suggests that before the isotherms intersect, $C_3H_8$ adsorption is dominating, however $CO_2$ adsorption dominates after the intersection point. FIG. 9B shows a comparison of experimental equilibrium data [17] of adsorbed $C_3H_8(1, \text{dots})-CO_2(2)$ binary mixture on zeolite H-Mordenite at 303 K and 41 kPa with IAST (dashed line) and RAST (solid line) results. FIG. 9C shows a comparison of experimental measurement of amount adsorbed [17] for $C_3H_8$ (1, blue dots), $CO_2$ (2, red dots) and total amount of the binary mixture adsorbed (black dots) on zeolite H-Mordenite at 303 K and 41 kPa with IAST (dashed line) and RAST (solid line) results. IAST fails to capture the azeotrope behavior as it could not determine the correct mole fractions in the adsorbate phase after the cross-over point. RAST with $\tau_{12}$=4.201, is able to qualitatively capture the azeotrope behavior. A plausible argument for the deviations between the experimental data and our model results is that the Sips isotherm does not accurately correlate the pure component isotherm data which leads to the deviations from experimental mixture adsorption data.

FIGS. 10A, 10B, and 10C are graphs showing another azeotrope exhibiting system on zeolite 13X. FIG. 10A shows that the Sips equation captures well the pure component isotherm data [35] for $iC_4H_{10}$ and $C_2H_4$ systems at 323 K. FIG. 10A shows a comparison of experimental pure component adsorption isotherm data [35] of $iC_4H_{10}$(1, blue dots) and $C_2H_4$(2, red dots) on zeolite 13X at 323 K with Sips isotherm correlations (solid line). Again, a similar phenomenon of intersection of pure component isotherms has been observed, thereby suggesting that an azeotrope-type behavior could be observed in binary mixture data. FIG. 10B shows a comparison of experimental equilibrium data [35] of adsorbed $iC_4H_{10}$(1, black dots)-$C_2H_4$(2) binary mixture on zeolite 13X at 323 K and 137.8 kPa with IAST (dashed line) and RAST (solid line) results. FIG. 10C shows a comparison of experimental measurement of amount adsorbed [35] for $iC_4H_{10}$ (1, blue dots), $C_2H_4$ (2, red dots) and total amount of the binary mixture adsorbed (black dots) on zeolite 13X at 323 K and 137.8 kPa with IAST (dashed line) and RAST (solid line) results. The IAST model fails to capture the azeotrope behavior whereas the RAST model, with $\tau_{12}$=2.084, semi-quantitatively captures the binary experimental data. Although not shown, azeotrope disappears at high temperature of 373 K and the RAST model also accurately represents the high temperature experimental data.

Multicomponent Mixture

The proposed new activity coefficient model is readily extendable to predict multicomponent adsorptions using the binary interaction parameters regressed from the binary mixture data. FIGS. 11A, 11B, 11C, and 11D are graphs showing the adsorbate phase composition predictions of the ternary system $C_2H_4(1)-C_3H_8(2)-CO_2(3)$ at 293 K and 53.3 kPa on zeolite 13X using the binary interaction parameters for the three binaries $C_2H_4(1)-C_3H_8(2)$, $C_2H_4(1)-CO_2(2)$ and $C_3H_8(1)-CO_2(2)$ [36] reported in Table 6. The dots represent experimental data [36] of the mole percent of each species in the adsorbate phase and the (dashed line) and (solid line) represent IAST and RAST predictions respectively. These figures show the comparison between IAST and RAST predictions at fixed vapor phase compositions of $C_2H_4$ and $C_3H_8$. It is observed that, for the four experimental data points available, the RAST predictions match well whereas the IAST predictions deviate much from the experimental results. This is because the $C_3H_8(1)-CO_2(2)$ binary forms an azeotrope and the IAST model fails to predict this behavior. To the contrary, FIGS. 11A, 11B, 11C, and 11D show that the activity coefficient model correctly predicts a slight curvature at various gas phase compositions, indicative of the non-ideal behavior of the ternary system.

FIG. 12 is a block diagram of a system 1200 in accordance with one embodiment of the present invention. The system 1200 for identifying activity coefficients for mixed-gas adsorption equilibrium in a gas adsorption system includes an input/output interface 1202, a memory 1202, and one or more processors 1206 communicably coupled to the input/output interface 1202 and the memory 1204. The one or more processors 1106 calculate a first gas activity coefficient $\gamma_1$ for a first gas using the one or more processors and a first equation comprising $$\ln\gamma_1 = \frac{x_2^2\tau_{12}[\exp(-\alpha\tau_{12})-1]}{[x_1\exp(-\alpha\tau_{12})+x_2]^2};$$

calculate a second gas activity coefficient $\gamma_2$ for a second gas using the one or more processors and a second equation comprising $$\ln\gamma_2 = \frac{x_1^2\tau_{21}[\exp(-\alpha\tau_{21})-1]}{[x_1+x_2\exp(-\alpha\tau_{21})]^2};$$

wherein: $x_1$ is a bulk mole fraction of the first gas, $x_2$ is a bulk mole fraction of the second gas, $\alpha$ is a first adjustable parameter, $\tau_{12}$ is derived by regression from mixture isotherm data and reflects a difference between adsorbate-adsorbent interactions of the first gas and the second gas, and $$\tau_{12} = -\tau_{21} = \left(\frac{g_{10}-g_{20}}{RT}\right),$$

$g_{10}$ is an interaction energy between molecules of the first gas and an adsorbent adsorption site, $g_{20}$ is an interaction energy between molecules of the second gas and an adsorbent adsorption site, R is the gas constant, and T is a temperature for the gas adsorption system; provide the first gas activity coefficient $\gamma_1$ for the first gas and the second gas activity coefficient $\gamma_2$ for the second gas to the input/output device; and use the first gas activity coefficient $\gamma_1$ for the first gas and the second gas activity coefficient $\gamma_2$ for the second gas in the gas adsorption system. Note that the one or more processors can be part of one or more controller, computers, servers or other devices suitable for performing the method. The memory can be any type of data storage. The input/output device can be any component capable of interfacing with the one or more processors. The components can be local, remote or a combination thereof. Moreover, the components can be part of a distributed computing architecture, design system or control system. In one aspect, the first gas or the second gas is polar. In another aspect, the first gas is $C_2H_4$ and the second gas is $C_2H_6$; the first gas is $C_2H_4$ and the second gas is $C_3H_6$; the first gas is $CO_2$ and the second gas is $C_2H_4$; or the first gas is $O_2$ and the second gas is $N_2$. In another aspect, the adsorbent adsorption site comprises activated carbon, silica gel, zeolite molecular sieve 13X, or zeolite molecular sieve 10X. In another aspect, the temperature is from 273 K to 323 K. In another aspect, a pressure for the gas adsorption system is from 10 kPa to 102 kPa. In another aspect, the gas adsorption system comprises an air separation system, a nitrogen rejection from methane system, or a carbon dioxide capture system. In another aspect, the input/output device comprises an interface to the gas adsorption system.

FIG. 13 shows a flowchart of a method 1300 in accordance with one embodiment of the present invention. The computerized method 1300 for identifying activity coefficients for mixed-gas adsorption equilibrium in a gas adsorption system includes: providing one or more processors, a memory communicably coupled to the one or more processors and an input/output device communicably coupled to the one or more processors in block 1302; calculating a first gas activity coefficient $\gamma_1$ for a first gas using the one or more processors and a first equation comprising $$\ln\gamma_1 = \frac{x_2^2 \tau_{12}[\exp(-\alpha\tau_{12}) - 1]}{[x_1 \exp(-\alpha\tau_{12}) + x_2]^2};$$

calculating a second gas activity coefficient $\gamma_2$ for a second gas using the one or more processors and a second equation comprising $$\ln\gamma_2 = \frac{x_1^2 \tau_{21}[\exp(-\alpha\tau_{21}) - 1]}{[x_1 + x_2 \exp(-\alpha\tau_{21})]^2}$$

in block 1304; wherein: $x_1$ is a bulk mole fraction of the first gas, $x_2$ is a bulk mole fraction of the second gas, $\alpha$ is a first adjustable parameter, $\tau_{12}$ is derived by regression from mixture isotherm data and reflects a difference between adsorbate-adsorbent interactions of the first gas and the second gas, and $$\tau_{12} = -\tau_{21} = \left(\frac{g_{10} - g_{20}}{RT}\right),$$

$g_{10}$ is an interaction energy between molecules of the first gas and an adsorbent adsorption site, $g_{20}$ is an interaction energy between molecules of the second gas and an adsorbent adsorption site, R is the gas constant, and T is a temperature for the gas adsorption system; providing the first gas activity coefficient $\gamma_1$ for the first gas and the second gas activity coefficient $\gamma_2$ for the second gas to the input/output device in block 1306; and using the first gas activity coefficient $\gamma_1$ for the first gas and the second gas activity coefficient $\gamma_2$ for the second gas in the gas adsorption system in block 1308. Note that the one or more processors can be part of one or more controller, computers, servers or other devices suitable for performing the method. The memory can be any type of data storage. The input/output device can be any component capable of interfacing with the one or more processors. The components can be local, remote or a combination thereof. Moreover, the components can be part of a distributed computing architecture, design system or control system. In one aspect, the first gas or the second gas is polar. In another aspect, the first gas is $C_2H_4$ and the second gas is $C_2H_6$; the first gas is $C_2H_4$ and the second gas is $C_3H_6$; the first gas is $CO_2$ and the second gas is $C_2H_4$; or the first gas is $O_2$ and the second gas is $N_2$. In another aspect, the adsorbent adsorption site comprises activated carbon, silica gel, zeolite molecular sieve 13X, or zeolite molecular sieve 10X. In another aspect, the temperature is from 273 K to 323 K. In another aspect, a pressure for the gas adsorption system is from 10 kPa to 102 kPa. In another aspect, the gas adsorption system comprises an air separation system, a nitrogen rejection from methane system, or a carbon dioxide capture system. In another aspect, the input/output device comprises an interface to the gas adsorption system.

The foregoing method can be implemented as a non-transitory computer readable medium. More specifically, a non-transitory computer readable medium containing program instructions that cause one or more processors to perform a method for identifying activity coefficients for mixed-gas adsorption equilibrium in a gas adsorption system includes: calculating a first gas activity coefficient $\gamma_1$ for a first gas using a first equation comprising $$\ln\gamma_1 = \frac{x_2^2 \tau_{12}[\exp(-\alpha\tau_{12}) - 1]}{[x_1 \exp(-\alpha\tau_{12}) + x_2]^2};$$

calculating a second gas activity coefficient $\gamma_2$ for a second gas using a second equation comprising $$\ln\gamma_2 = \frac{x_1^2 \tau_{21}[\exp(-\alpha\tau_{21}) - 1]}{[x_1 + x_2 \exp(-\alpha\tau_{21})]^2};$$

wherein: $x_1$ is a bulk mole fraction of the first gas, $x_2$ is a bulk mole fraction of the second gas, $\alpha$ is a first adjustable parameter, $\tau_{12}$ is derived by regression from mixture isotherm data and reflects a difference between adsorbate-adsorbent interactions of the first gas and the second gas, and $$\tau_{12} = -\tau_{21} = \left(\frac{g_{10} - g_{20}}{RT}\right),$$

$g_{10}$ is an interaction energy between molecules of the first gas and an adsorbent adsorption site, $g_{20}$ is an interaction energy between molecules of the second gas and an adsorbent adsorption site, R is the gas constant, and T is a temperature for the gas adsorption system; providing the first gas activity coefficient $\gamma_1$ for the first gas and the second gas activity coefficient $\gamma_2$ for the second gas to an input/output device communicably coupled to the one or more processors; and using the first gas activity coefficient $\gamma_1$ for the first gas and the second gas activity coefficient $\gamma_2$ for the second gas in the gas adsorption system. In one aspect, the first gas or the second gas is polar. In another aspect, the first gas is $C_2H_4$ and the second gas is $C_2H_6$; the first gas is $C_2H_4$ and the second gas is $C_3H_6$; the first gas is $CO_2$ and the second gas is $C_2H_4$; or the first gas is $O_2$ and the second gas is $N_2$. In another aspect, the adsorbent adsorption site comprises activated carbon, silica gel, zeolite molecular sieve 13X, or zeolite molecular sieve 10X. In another aspect, the temperature is from 273 K to 323 K. In another aspect, a pressure for the gas adsorption system is from 10 kPa to 102 kPa. In another aspect, the gas adsorption system comprises an air separation system, a nitrogen rejection from methane system, or a carbon dioxide capture system. In another aspect, the input/output device comprises an interface to the gas adsorption system.

One skilled in the art of mixed-gas adsorption will recognize that the present invention provide sufficiently accurate activity coefficients for mixed-gas adsorption equilibrium for predictions with sufficient accuracy for rigorous adsorption design for systems of industrial interest.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of" As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step, or a limitation) or group of integers (e.g., feature(s), element(s), characteristic(s), property(ies), method/process(s) steps, or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about," "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the devices and/or methods disclosed and claimed herein can be made and executed without undue experimentation in light of the present disclosure. While the devices and/or methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope, and concept of the invention as defined by the appended claims.

Furthermore, no limitations are intended to the details of construction or design herein shown, other than as described in the claims below. It is therefore evident that the particular embodiments disclosed above may be altered or modified and all such variations are considered within the scope and spirit of the disclosure. Accordingly, the protection sought herein is as set forth in the claims below.

Modifications, additions, or omissions may be made to the systems and apparatuses described herein without departing from the scope of the invention. The components of the systems and apparatuses may be integrated or separated. Moreover, the operations of the systems and apparatuses may be performed by more, fewer, or other components. The methods may include more, fewer, or other steps. Additionally, steps may be performed in any suitable order.

To aid the Patent Office, and any readers of any patent issued on this application in interpreting the claims appended hereto, applicants wish to note that they do not intend any of the appended claims to invoke 35 U.S.C. § 112(f) as it exists on the date of filing hereof unless the words "means for" or "step for" are explicitly used in the particular claim.

REFERENCES

1. I. Langmuir, "The adsorption of gases on plane surfaces of glass, mica and platinum," *Journal of the American Chemical society*, vol. 40, pp. 1361-1403, 1918.
2. S. Bartholdy, M. G. Bjørner, E. Solbraa, A. Shapiro, and G. M. Kontogeorgis, "Capabilities and limitations of predictive engineering theories for multicomponent adsorption," *Industrial & Engineering Chemistry Research*, vol. 52, pp. 11552-11563, 2013.

3. A. L. Myers and J. M. Prausnitz, "Thermodynamics of mixed-gas adsorption," *AIChE Journal*, vol. 11, pp. 121-127, 1965.

4. S. Sircar and A. L. Myers, "Surface potential theory of multilayer adsorption from gas mixtures," *Chemical Engineering Science*, vol. 28, pp. 489-499, 1973.

5. M. Sakuth, J. Meyer, and J. Gmehling, "Measurement and prediction of binary adsorption equilibria of vapors on dealuminated Y-zeolites (DAY)," *Chemical Engineering and Processing: Process Intensification*, vol. 37, pp. 267-277, 1998.

6. S. Suwanayuen and R. P. Danner, "Vacancy solution theory of adsorption from gas mixtures," *AIChE Journal*, vol. 26, pp. 76-83, 1980.

7. M. Polanyi, "Adsorption von Gasen (Dampfen) durch ein festes nichtfluchtiges Adsorbens," *Verhandlungen der Deutschen Physekalischen Gesellschaft*, vol. 18, pp. 55-80, 1916.

8. M. M. i. Dubinin, "Physical adsorption of gases and vapors in micropores," in *Progress in surface and membrane science*. vol. 9, ed: Elsevier, 1975, pp. 1-70.

9. M. M. Dubinin, "Fundamentals of the theory of adsorption in micropores of carbon adsorbents: characteristics of their adsorption properties and microporous structures," *Pure and Applied Chemistry*, vol. 61, pp. 1841-1843, 1989.

10. A. A. Shapiro and E. H. Stenby, "Potential theory of multicomponent adsorption," *Journal of Colloid and Interface Science*, vol. 201, pp. 146-157, 1998.

11. D. M. Ruthven, "Simple theoretical adsorption isotherm for zeolites," *Nature Physical Science*, vol. 232, p. 70, 1971.

12. A. Martinez, M. Castro, C. McCabe, and A. Gil-Villegas, "Predicting adsorption isotherms using a two-dimensional statistical associating fluid theory," *The Journal of chemical physics*, vol. 126, p. 074707, 2007.

13. K. S. Walton and D. S. Sholl, "Predicting multicomponent adsorption: 50 years of the ideal adsorbed solution theory," *AIChE Journal*, vol. 61, pp. 2757-2762, 2015.

14. A. L. Myers, "Activity coefficients of mixtures adsorbed on heterogeneous surfaces," *AIChE journal*, vol. 29, pp. 691-693, 1983.

15. J. Dunne and A. L. Myers, "Adsorption of gas mixtures in micropores: effect of difference in size of adsorbate molecules," *Chemical engineering science*, vol. 49, pp. 2941-2951, 1994.

16. E. Costa, J. L. Sotelo, G. Calleja, and C. Marron, "Adsorption of binary and ternary hydrocarbon gas mixtures on activated carbon: experimental determination and theoretical prediction of the ternary equilibrium data," *AIChE Journal*, vol. 27, pp. 5-12, 1981.

17. O. Talu and I. Zwiebel, "Multicomponent adsorption equilibria of nonideal mixtures," *AIChE journal*, vol. 32, pp. 1263-1276, 1986.

18. S. Sochard, N. Fernandes, and J. M. Reneaume, "Modeling of adsorption isotherm of a binary mixture with real adsorbed solution theory and nonrandom two-liquid model," *AIChE journal*, vol. 56, pp. 3109-3119, 2010.

19. D. G. Steffan and A. Akgerman, "Thermodynamic modeling of binary and ternary adsorption on silica gel," *AIChE journal*, vol. 47, pp. 1234-1246, 2001.

20. O. Talu and I. Zwiebel, "Spreading pressure dependent equation for adsorbate phase activity coefficients," *Reactive Polymers, Ion Exchangers, Sorbents*, vol. 5, pp. 81-91, 1987.

21. H. Renon and J. M. Prausnitz, "Local compositions in thermodynamic excess functions for liquid mixtures," *AIChE journal*, vol. 14, pp. 135-144, 1968.

22. A. Ravichandran, R. Khare, and C. C. Chen, "Predicting NRTL binary interaction parameters from molecular simulations," *AIChE Journal*, 2018.

23. R. L. Scott, "Corresponding states treatment of nonelectrolyte solutions," *The Journal of Chemical Physics*, vol. 25, pp. 193-205, 1956.

24. F. R. Siperstein and A. L. Myers, "Mixed-gas adsorption," *AIChE journal*, vol. 47, pp. 1141-1159, 2001.

25. D. D. Do, *Adsorption analysis: equilibria and kinetics* vol. 2: Imperial college press London, 1998.

26. E. Costa, G. Calleja, C. Marron, A. Jimenez, and J. Pau, "Equilibrium adsorption of methane, ethane, ethylene, and propylene and their mixtures on activated carbon," *Journal of Chemical and Engineering Data*, vol. 34, pp. 156-160, 1989.

27. R. T. Yang, *Gas separation by adsorption processes*: Butterworth-Heinemann, 2013.

28. W. K. Lewis, E. R. Gilliland, B. Chertow, and W. H. Hoffman, "Vapor—adsorbate1 equilibrium. I. propane—propylene on activated carbon and on silica gel," *Journal of the American Chemical Society*, vol. 72, pp. 1153-1157, 1950.

29. W. K. Lewis, E. R. Gilliland, B. Chertow, and W. Milliken, "Vapor—Adsorbate Equilibrium. II. Acetylene—Ethylene on Activated Carbon and on Silica Gel," *Journal of the American Chemical Society*, vol. 72, pp. 1157-1159, 1950.

30. W. K. Lewis, E. R. Gilliland, B. Chertow, and D. Bareis, "Vapor—Adsorbate Equilibrium. III. The Effect of Temperature on the Binary Systems Ethylene—Propane, Ethylene—Propylene over Silica Gel," *Journal of the American Chemical Society*, vol. 72, pp. 1160-1163, 1950.

31. E. C. Markham and A. F. Benton, "The adsorption of gas mixtures by silica," *Journal of the American Chemical Society*, vol. 53, pp. 497-507, 1931.

32. R. P. Danner and L. A. Wenzel, "Adsorption of carbon monoxide-nitrogen, carbon monoxide-oxygen, and oxygen-nitrogen mixtures on synthetic zeolites," *AIChE Journal*, vol. 15, pp. 515-520, 1969.

33. G. Calleja, J. Pau, and J. A. Calles, "Pure and multi-component adsorption equilibrium of carbon dioxide, ethylene, and propane on ZSM-5 zeolites with different Si/Al ratios," *Journal of Chemical & Engineering Data*, vol. 43, pp. 994-1003, 1998.

34. J. T. Nolan, T. W. McKeehan, and R. P. Danner, "Equilibrium adsorption of oxygen, nitrogen, carbon monoxide, and their binary mixtures on molecular sieve type 10X," *Journal of Chemical and Engineering Data*, vol. 26, pp. 112-115, 1981.

35. S. H. Hyun and R. P. Danner, "Equilibrium adsorption of ethane, ethylene, isobutane, carbon dioxide, and their binary mixtures on 13X molecular sieves," *Journal of Chemical and Engineering Data*, vol. 27, pp. 196-200, 1982.

36. G. Calleja, A. Jimenez, J. Pau, L. Dominguez, and P. Perez, "Multicomponent adsorption equilibrium of ethylene, propane, propylene and CO2 on 13X zeolite," *Gas separation & purification*, vol. 8, pp. 247-256, 1994.

What is claimed is:

1. A computerized method for identifying activity coefficients for mixed-gas adsorption equilibrium in a gas adsorption system comprising:

providing one or more processors, a memory communicably coupled to the one or more processors and an input/output device communicably coupled to the one or more processors;

calculating a first gas activity coefficient $\gamma_1$ for a first gas using the one or more processors and a first equation comprising $$\ln \gamma_1 = \frac{x_2^2 \tau_{12}[\exp(-\alpha \tau_{12}) - 1]}{[x_1 \exp(-\alpha \tau_{12}) + x_2]^2};$$

calculating a second gas activity coefficient $\gamma_2$ for a second gas using the one or more processors and a second equation comprising $$\ln \gamma_2 = \frac{x_1^2 \tau_{21}[\exp(-\alpha \tau_{21}) - 1]}{[x_1 + x_2 \exp(-\alpha \tau_{21})]^2};$$

wherein: $x_1$ is a bulk mole fraction of the first gas,
$x_2$ is a bulk mole fraction of the second gas,
$\alpha$ is a first adjustable parameter,
$\tau_{12}$ is derived by regression from mixture isotherm data and reflects a difference between adsorbate-adsorbent interactions of the first gas and the second gas, and $$\tau_{12} = -\tau_{21} = \left(\frac{g_{10} - g_{20}}{RT}\right),$$

$g_{10}$ is an interaction energy between molecules of the first gas and an adsorbent adsorption site,
$g_{20}$ is an interaction energy between molecules of the second gas and an adsorbent adsorption site,
R is the gas constant, and
T is a temperature for the gas adsorption system;
providing the first gas activity coefficient $\gamma_1$ for the first gas and the second gas activity coefficient $\gamma_2$ for the second gas to the input/output device; and
configuring the gas adsorption system using the first gas activity coefficient $\gamma_1$ for the first gas and the second gas activity coefficient $\gamma_2$ for the second gas.

2. The method of claim 1, wherein the first gas or the second gas is polar.

3. The method of claim 1, wherein:
the first gas is $C_2H_4$ and the second gas is $C_2H_6$;
the first gas is $C_2H_4$ and the second gas is $C_3H_6$;
the first gas is $CO_2$ and the second gas is $C_2H_4$; or
the first gas is $O_2$ and the second gas is $N_2$.

4. The method of claim 1, wherein the adsorbent adsorption site comprises activated carbon, silica gel, zeolite molecular sieve 13X, or zeolite molecular sieve 10X.

5. The method of claim 1, wherein the temperature is from 273 K to 323 K.

6. The method of claim 1, wherein a pressure for the gas adsorption system is from 10 kPa to 102 kPa.

7. The method of claim 1, wherein the gas adsorption system comprises an air separation system, a nitrogen rejection from methane system, or a carbon dioxide capture system.

8. The method of claim 1, wherein the input/output device comprises an interface to the gas adsorption system.

9. A non-transitory computer readable medium containing program instructions that cause one or more processors to perform a method for identifying activity coefficients for mixed-gas adsorption equilibrium in a gas adsorption system comprising:

calculating a first gas activity coefficient $\gamma_1$ for a first gas using a first equation comprising $$\ln \gamma_1 = \frac{x_2^2 \tau_{12}[\exp(-\alpha \tau_{12}) - 1]}{[x_1 \exp(-\alpha \tau_{12}) + x_2]^2};$$

calculating a second gas activity coefficient $\gamma_2$ for a second gas using a second equation comprising $$\ln \gamma_2 = \frac{x_1^2 \tau_{21}[\exp(-\alpha \tau_{21}) - 1]}{[x_1 + x_2 \exp(-\alpha \tau_{21})]^2};$$

wherein: $x_1$ is a bulk mole fraction of the first gas,
$x_2$ is a bulk mole fraction of the second gas,
$\alpha$ is a first adjustable parameter,
$\tau_{12}$ is derived by regression from mixture isotherm data and reflects a difference between adsorbate-adsorbent interactions of the first gas and the second gas, and $$\tau_{12} = -\tau_{21} = \left(\frac{g_{10} - g_{20}}{RT}\right),$$

$g_{10}$ is an interaction energy between molecules of the first gas and an adsorbent adsorption site,
$g_{20}$ is an interaction energy between molecules of the second gas and an adsorbent adsorption site,
R is the gas constant, and
T is a temperature for the gas adsorption system;
providing the first gas activity coefficient $\gamma_1$ for the first gas and the second gas activity coefficient $\gamma_2$ for the second gas to an input/output device communicably coupled to the one or more processors; and
configuring the gas adsorption system using the first gas activity coefficient $\gamma_1$ for the first gas and the second gas activity coefficient $\gamma_2$ for the second gas in the gas adsorption system.

10. The non-transitory computer readable medium of claim 9, wherein the first gas or the second gas is polar.

11. The non-transitory computer readable medium of claim 9, wherein:
the first gas is $C_2H_4$ and the second gas is $C_2H_6$;
the first gas is $C_2H_4$ and the second gas is $C_3H_6$;
the first gas is $CO_2$ and the second gas is $C_2H_4$; or
the first gas is $O_2$ and the second gas is $N_2$.

12. The non-transitory computer readable medium of claim 9, wherein the adsorbent adsorption site comprises activated carbon, silica gel, zeolite molecular sieve 13X, or zeolite molecular sieve 10X.

13. The non-transitory computer readable medium of claim 9, wherein the temperature is from 273 K to 323 K.

14. The non-transitory computer readable medium of claim 9, wherein a pressure for the gas adsorption system is from 10 kPa to 102 kPa.

15. The non-transitory computer readable medium of claim 9, wherein the gas adsorption system comprises an air separation system, a nitrogen rejection from methane system, or a carbon dioxide capture system.

16. The non-transitory computer readable medium of claim 9, wherein the input/output device comprises an interface to the gas adsorption system.

17. A system for identifying activity coefficients for mixed-gas adsorption equilibrium in a gas adsorption system comprising:
a memory;
an input/output device; and
one or more processors communicably coupled to the memory and the input/output device, wherein the one or more processors:
calculate a first gas activity coefficient $\gamma_1$ for a first gas using the one or more processors and a first equation comprising $$\ln\gamma_1 = \frac{x_2^2 \tau_{12}[\exp(-\alpha\tau_{12}) - 1]}{[x_1 \exp(-\alpha\tau_{12}) + x_2]^2};$$

calculate a second gas activity coefficient $\gamma_2$ for a second gas using the one or more processors and a second equation comprising $$\ln\gamma_2 = \frac{x_1^2 \tau_{21}[\exp(-\alpha\tau_{21}) - 1]}{[x_1 + x_2 \exp(-\alpha\tau_{21})]^2};$$

wherein: $x_1$ is a bulk mole fraction of the first gas,
$x_2$ is a bulk mole fraction of the second gas,
$\alpha$ is a first adjustable parameter,
$\tau_{12}$ is derived by regression from mixture isotherm data and reflects a difference between adsorbate-adsorbent interactions of the first gas and the second gas, and $$\tau_{12} = -\tau_{21} = \left(\frac{g_{10} - g_{20}}{RT}\right),$$

$g_{10}$ is an interaction energy between molecules of the first gas and an adsorbent adsorption site,
$g_{20}$ is an interaction energy between molecules of the second gas and an adsorbent adsorption site,
R is the gas constant, and
T is a temperature for the gas adsorption system;
provide the first gas activity coefficient $\gamma_1$ for the first gas and the second gas activity coefficient $\gamma_2$ for the second gas to the input/output device; and
wherein the gas adsorption system is configured using the first gas activity coefficient $\gamma_1$ for the first gas and the second gas activity coefficient $\gamma_2$ for the second gas in the gas adsorption system.

18. The system of claim 17, wherein the first gas or the second gas is polar.

19. The system of claim 17, wherein:
the first gas is $C_2H_4$ and the second gas is $C_2H_6$;
the first gas is $C_2H_4$ and the second gas is $C_3H_6$;
the first gas is $CO_2$ and the second gas is $C_2H_4$; or
the first gas is $O_2$ and the second gas is $N_2$.

20. The system of claim 17, wherein the adsorbent adsorption site comprises activated carbon, silica gel, zeolite molecular sieve 13X, or zeolite molecular sieve 10X.

21. The system of claim 17, wherein the temperature is from 273 K to 323 K.

22. The system of claim 17, wherein a pressure for the gas adsorption system is from 10 kPa to 102 kPa.

23. The system of claim 17, wherein the gas adsorption system comprises an air separation system, a nitrogen rejection from methane system, or a carbon dioxide capture system.

24. The system of claim 17, wherein the input/output device comprises an interface to the gas adsorption system.

* * * * *